(12) United States Patent
Mühlebach et al.

(10) Patent No.: US 7,595,359 B2
(45) Date of Patent: Sep. 29, 2009

(54) CATIONIC ALKOXYAMINES AND THEIR USE IN PRODUCING NANO PARTICLES FROM NATURAL OR SYNTHETIC CLAYS

(75) Inventors: Andreas Mühlebach, Frick (CH); Peter Nesvadba, Marly (CH); Andreas Kramer, Meyriez (CH)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 771 days.

(21) Appl. No.: 10/519,030

(22) PCT Filed: Jun. 17, 2003

(86) PCT No.: PCT/EP03/06370

§ 371 (c)(1),
(2), (4) Date: Dec. 22, 2004

(87) PCT Pub. No.: WO04/000809

PCT Pub. Date: Dec. 31, 2003

(65) Prior Publication Data

US 2005/0215691 A1 Sep. 29, 2005

(30) Foreign Application Priority Data

Jun. 24, 2002 (EP) .................................. 02405520

(51) Int. Cl.
*C08K 3/34* (2006.01)
(52) U.S. Cl. ...................... 524/445; 524/447; 501/145; 501/147
(58) Field of Classification Search ................. 524/445
See application file for complete search history.

(56) References Cited

U.S. PATENT DOCUMENTS

| | | | | |
|---|---|---|---|---|
| 4,972,009 A | * | 11/1990 | Suhadolnik et al. ........... 524/99 |
| 5,004,770 A | * | 4/1991 | Cortolano et al. ............. 524/93 |
| 5,096,950 A | * | 3/1992 | Galbo et al. ................... 524/99 |
| 5,204,473 A | * | 4/1993 | Winter et al. ................ 546/188 |
| 5,627,248 A | * | 5/1997 | Koster et al. ................. 526/217 |
| H1957 H | * | 4/2001 | Fried et al. .................... 526/82 |
| 6,492,521 B2 | * | 12/2002 | Sassi et al. .................... 546/188 |
| 6,559,207 B1 | * | 5/2003 | English et al. ............... 524/102 |
| 6,569,940 B1 | * | 5/2003 | Wunderlich et al. ......... 524/718 |
| 6,696,570 B2 | * | 2/2004 | Sassi et al. .................... 546/188 |
| 6,727,300 B2 | * | 4/2004 | Sassi ........................... 524/103 |
| 6,872,832 B2 | * | 3/2005 | Galbo et al. ................... 546/207 |
| 6,881,773 B2 | * | 4/2005 | Zingg et al. ................... 524/100 |
| 6,967,252 B2 | * | 11/2005 | Troutman et al. ............ 546/201 |
| 7,109,260 B2 | * | 9/2006 | Kaprinidis et al. ............ 524/99 |
| 7,214,729 B2 | * | 5/2007 | Kaprinidis et al. .......... 524/100 |
| 7,323,502 B2 | * | 1/2008 | Kaprinidis ..................... 524/95 |
| 7,361,755 B2 | * | 4/2008 | Pastor et al. ..................... 544/1 |

FOREIGN PATENT DOCUMENTS

WO 02/24756 3/2002

OTHER PUBLICATIONS

Giannelis et al. "Direct Synthesis of Dispersed Nanocomposites by In Situ Living Free Radical Polymerization Using a Silicate-Anchored Initiator" J. Am. Chem. Soc. 1999, 121, 1615-1616.*
Miura et al. "High0Yield Synthesis of Functionalized Alkoxy Amines Initiators and Approach to Well Controlled Block Copolymers Using Them" Macromolecules, 1999, 32, 8356-8362.*
M. Weimer et al., J. Am. Chem. Soc., vol. 121, (1999), pp. 1615-1616.
H. Böttcher et al., J. Mater. Chem. (2002), vol. 12, pp. 1351-1354.
U. Velten et al., Macromolecules, vol. 32, No. 11, pp. 3590-3597.

* cited by examiner

*Primary Examiner*—Katarzyna Wyrozebski
(74) *Attorney, Agent, or Firm*—Joseph C. Suhadolnik

(57) ABSTRACT

The instant invention relates to cationic alkoxyamines, which are useful as polymerization initiators/regulators in a controlled stable free radical polymerization process to produce intercalated and/or exfoliated nanoparticles from natural or synthetic clays. The invention also relates to improved nanocomposites produced by this process and to the use of these nanocomposite compositions as, for example, coatings, sealants, caulks, adhesives and as plastic additives.

18 Claims, No Drawings

CATIONIC ALKOXYAMINES AND THEIR USE IN PRODUCING NANO PARTICLES FROM NATURAL OR SYNTHETIC CLAYS

The instant invention relates to cationic alkoxyamines, which are useful as polymerization initiators/regulators in a controlled free radical polymerization process to produce intercalated and/or exfoliated nanoparticles from natural or synthetic clays. The invention also relates to improved nanocomposite compositions produced by this process and to the use of these nanocomposite compositions as, for example, coatings, sealants, caulks, adhesives and as plastic additives.

One way of improving polymer properties is by adding a natural or synthetic clay material to polymers to form composite materials. However, incorporating clays into polymers may not provide a desirable improvement in the physical properties, particularly mechanical and optical properties of the polymer may be adversely affected.

Nanonocomposite compositions containing finely dispersed natural or synthetic clay with at least partially intercalated and/or exfoliated layers and mixtures of ethylenically unsaturated monomers and/or polymers therefrom have therefore attracted much interest in the last years. These materials combine the desired effects of dispersed clay by avoiding the negative influence on, for example, the mechanical or optical properties.

Such compositions, methods for making them and their use in polymers and coatings are for example described in WO 02/24759. Polymerization processes are described using montmorillonite clay, acrylate monomers and for example ammonium persulfate as radical initiator. This conventional polymerization process leads to polymers with broad molecular weight distributions and a high polydispersity index (PD).

Y. Sogah et al., J. Am. Chem. Soc. 1999, 121, 1615-1616 describe the synthesis of dispersed nanocomposite compositions by in situ living free radical polymerization of styrene using a silicate-anchored initiator. The nitroxyl compound used is a 2,2,6,6 tetramethyl-piperidine alkoxyamine. Although Sogah et al. have shown the principal possibility of preparing nanocomposite compositions by controlled free radical polymerization, they have been limited to styrene, since the known initiators/regulators are not efficient enough to polymerize acrylates or methacrylates with reasonable conversion rates at acceptable temperatures.

The present invention provides alkoxyamines, which can be anchored to natural or synthetic clays by a cationic anchor group and which have a high reactivity towards acrylates, methacrylates, styrene and other monomers resulting in a controlled molecular weight with narrow molecular weight distribution. With these compounds polymerization leads to high monomer to polymer conversions in short times and at relatively low temperatures.

In contrast to conventional radical polymerization, controlled radical polymerization allows to adjust the molecular weight of all growing chains almost uniformly to a predetermined length (low polydispersity), resulting in an almost ideal dispersion of the intercalated and/or exfoliated clay particles.

The nanocomposite compositions of the instant invention can be optically almost transparent, indicating the fine distribution, on the nanometer scale, of the clay.

One aspect of the invention is a compound of formula (I) or (II)

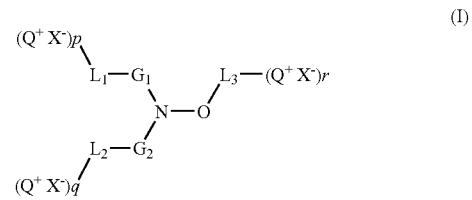

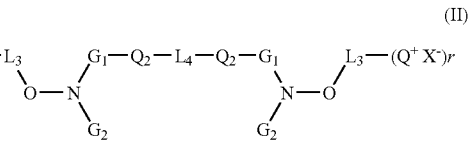

wherein $G_1$ and $G_2$ independently represent a tertiary carbon atom to which unsubstituted $C_1$-$C_{18}$alkyl or phenyl or with CN, $COC_1$-$C_{18}$alkyl, CO-phenyl, $COOC_1$-$C_{18}$alkyl, $OC_1$-$C_{18}$alkyl, $NO_2$, $NHC_1$-$C_{18}$alkyl or $N(C_1$-$C_{18})_2$alkyl substituted alkyl or phenyl groups are bonded; or one of $G_1$ and $G_2$ is a secondary carbon atom to which a group —$P(O)(OR_{22})_2$ and the other is as defined above; or $G_1$ and $G_2$ together with the nitrogen atom to which they are bonded to form a 5 to 8 membered heterocyclic ring or a polycyclic or spirocyclic 5 to 20 membered heterocyclic ring system, which is substituted with 4 $C_1$-$C_4$alkyl groups or 2 $C_5$-$C_{12}$ spirocycloalkyl groups in ortho position to the nitrogen atom and which may be further substituted with one or more $C_1$-$C_{18}$alkyl, $C_1$-$C_{18}$alkoxy or =O groups; and which may be interrupted by a further oxygen or nitrogen atom;

with the proviso that at least one of the 4 $C_1$-$C_4$alkyl groups in ortho position to the nitrogen atom is higher alkyl than methyl;

$L_1$, $L_2$ and $L_4$ is a linking group selected from the group consisting of a direct bond, $R_1$—Y or $R_2$—C(O)—Y— where Y is attached to $G_1$ and/or $G_2$; $C_1$-$C_{25}$alkylene, $C_2$-$C_{25}$alkylene interrupted by

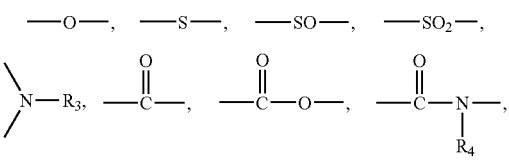

phenylene and $C_5$-$C_8$cycloalkylene;

Y is O, or $NR_9$ $L_3$ is a group containing at least one carbon atom and is such that the radical .$L_3$—($Q^+X^-$) derived from the group is able to initiate polymerization of ethylenically unsaturated monomers;

$Q_2$ is a direct bond, O, $NR_5$ or $NR_5R_6$;

$Q^+$ is a cationic group selected from the group consisting of

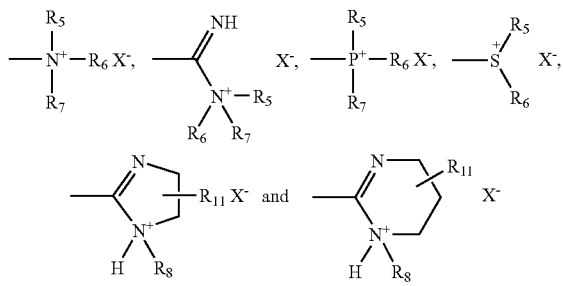

wherein $R_1$ is $C_1$-$C_{18}$alkylene, $R_2$ is a direct bond or $C_1$-$C_{18}$alkylene, $R_3$ is hydrogen or $C_1$-$C_{18}$alkyl, $R_4$ is hydrogen or $C_1$-$C_{18}$alkyl, $R_5$, $R_6$ and $R_7$ are each independently of the others hydrogen, $C_1$-$C_{18}$alkyl, $C_3$-$C_{12}$cycloalkyl, phenyl or $C_7$-$C_9$phenylalkyl or $C_6$-$C_{10}$heteroaryl which all may be unsubstituted or substituted by halogen, OH, $NO_2$, CN, $C_1$-$C_4$alkoxy, or $R_5$, $R_6$ and $R_7$ together with the nitrogen or phosphor atom to which they are bonded form a 3-12 membered monocyclic or polycyclic ring, which may contain further heteroatoms;

$R_8$ is hydrogen or $C_1$-$C_{25}$alkyl, $C_3$-$C_{25}$alkyl interrupted by oxygen, sulfur or by

or $C_2$-$C_{24}$alkenyl, $R_9$ is hydrogen, $C_1$-$C_{18}$alkyl, $C_3$-$C_{18}$alkenyl, $C_3$-$C_{18}$alkinyl, phenyl, $C_7$-$C_9$phenylalkyl, which all may be unsubstituted or substituted by one or more hydroxy, halogen or $C_1$-$C_4$alkoxy groups;

$R_{22}$ is $C_1$-$C_{18}$alkyl;

$X^-$ is the anion of a $C_1$-$C_{18}$carboxylic acid which may contain more than one carboxylic acid group, fluoride, chloride, bromide, iodide, nitrite, nitrate, hydroxide, acetate, hydrogen sulfate, sulfate, $C_1$-$C_{18}$alkoxy sulfate, aromatic or aliphatic sulfonate, carbonate, hydrogen carbonate, perchlorate, chlorate, tetrafluoroborate, borate, phosphate, hydrogenphosphate, dihydrogenphosphate or mixtures thereof; and p, q, and r are independently of each other a number from 0 to 10 and at least one is different from 0.

Alkyl having up to 18 carbon atoms is a branched or unbranched radical, for example methyl, ethyl, propyl, isopropyl, n-butyl, sec-butyl, isobutyl, tert-butyl, 2-ethylbutyl, n-pentyl, isopentyl, 1-methylpentyl, 1,3-dimethylbutyl, n-hexyl, 1-methylhexyl, n-heptyl, isoheptyl, 1,1,3,3-tetramethylbutyl, 1-methylheptyl, 3-methylheptyl, n-octyl, 2-ethylhexyl, 1,1,3-trimethylhexyl, 1,1,3,3-tetramethylpentyl, nonyl, decyl, undecyl, 1-methylundecyl, dodecyl, 1,1,3,3,5,5-hexamethylhexyl, tridecyl, tetradecyl, pentadecyl, hexadecyl, heptadecyl or octadecyl.

$C_3$-$C_{18}$Alkyl interrupted by oxygen, sulfur or by

is, for example, $CH_3-O-CH_2CH_2-$, $CH_3-S-CH_2CH_2-$, $CH_3-N(CH_3)-CH_2CH_2-$, $CH_3-O-CH_2CH_2-O-CH_2CH_2-$, $CH_3-(O-CH_2CH_2-)_2O-CH_2CH_2-$, $CH_3-(O-CH_2CH_2-)_3O-CH_2CH_2-$ or $CH_3-(O-CH_2CH_2-)_4O-CH_2CH_2-$.

$C_7$-$C_9$Phenylalkyl is, for example, benzyl, α-methylbenzyl, α,α-dimethylbenzyl or 2-phenylethyl. Preference is given to benzyl and α,α-dimethylbenzyl.

$C_1$-$C_{25}$Alkylene is a branched or unbranched radical, for example methylene, ethylene, propylene, trimethylene, tetramethylene, pentamethylene, hexamethylene, heptamethylene, octamethylene, decamethylene, dodecamethylene or octadecamethylene.

$C_2$-$C_{25}$alkylene interrupted by

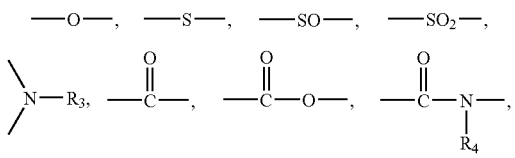

phenylene or $C_5$-$C_8$cycloalkylene is, for example,

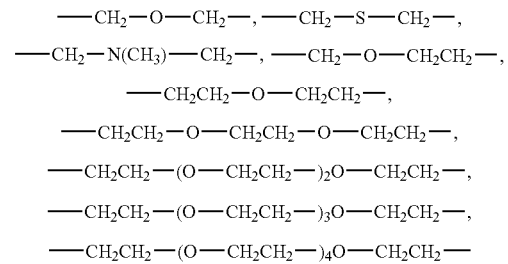

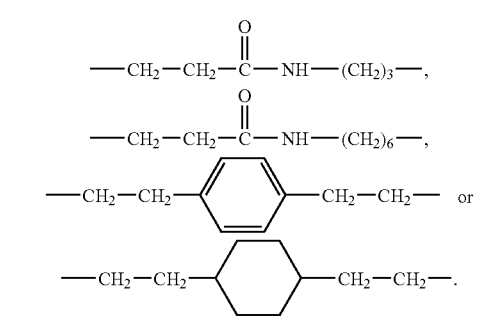

Alkenyl having 2 to 24 carbon atoms is a branched or unbranched radical such as, for example, vinyl, propenyl, 2-butenyl, 3-butenyl, isobutenyl, n-2,4-pentadienyl, 3-methyl-2-butenyl, n-2-octenyl, n-2-dodecenyl, iso-dodecenyl, oleyl, n-2-octadecenyl or n-4-octadecenyl. Preference is given to alkenyl having 3 to 18, especially 3 to 12, for example 3 to 6, especially 3 to 4 carbon atoms.

Alkinyl having from 3 to 18 carbon atoms is a branched or unbranched radical, for example propinyl, 2-butinyl, 3-butinyl, isobutinyl, n-2,4-pentadiinyl, 3-methyl-2-butinyl, n-2-octinyl, n-2-dodecinyl, isododecinyl.

Halogen is, for example, chlorine, bromine or iodine. Preference is given to chlorine and bromine.

Alkoxy having up to 25 carbon atoms is a branched or unbranched radical, for example methoxy, ethoxy, propoxy, isopropoxy, n-butoxy, isobutoxy, pentyloxy, isopentyloxy, hexyloxy, heptyloxy, octyloxy, decyloxy, tetradecyloxy, hexadecyloxy or octadecyloxy. Preference is given to alkoxy having from 1 to 12, especially from 1 to 8, e.g. from 1 to 6, carbon atoms.

Alkanoyloxy having up to 25 carbon atoms is a branched or unbranched radical, for example acetoxy, propionyloxy, butanoyloxy, pentanoyloxy, hexanoyloxy, heptanoyloxy, octanoyloxy, nonanoyloxy, decanoyloxy, undecanoyloxy, dodecanoyloxy, tridecanoyloxy, tetradecanoyloxy, pentadecanoyloxy, hexadecanoyloxy, heptadecanoyloxy, octadecanoyloxy, icosanoyloxy or docosanoyloxy. Preference is given to alkanoyloxy having from 2 to 18, especially from 2 to 12, e.g. from 2 to 6, carbon atoms.

Hydroxyl-substituted $C_2$-$C_{18}$alkyl is a branched or unbranched radical which contains preferably 1 to 3, in particular 1 or 2, hydroxyl groups, such as, for example, hydroxyethyl, 3-hydroxypropyl, 2-hydroxypropyl, 4-hydroxybutyl, 3-hydroxybutyl, 2-hydroxybutyl, 5-hydroxypentyl, 4-hydroxypentyl, 3-hydroxypentyl, 2-hydroxypentyl, 6-hydroxyhexyl, 5-hydroxyhexyl, 4-hydroxyhexyl, 3-hydroxyhexyl, 2-hydroxyhexyl, 7-hydroxyheptyl, 6-hydroxyheptyl, 5-hydroxyheptyl, 4-hydroxyheptyl, 3-hydroxyheptyl, 2-hydroxyheptyl, 8-hydroxyoctyl, 7-hydroxyoctyl, 6-hydroxyoctyl, 5-hydroxyoctyl, 4-hydroxyoctyl, 3-hydroxyoctyl, 2-hydroxyoctyl, 9-hydroxynonyl, 10-hydroxydecyl, 11-hydroxyundecyl, 12-hydroxydodecyl, 13-hydroxytridecyl, 14-hydroxytetradecyl, 15-hydroxypentadecyl, 16-hydroxyhexadecyl, 17-hydroxyheptadecyl, 18-hydroxyoctadecyl.

$C_5$-$C_{12}$cycloalkyl is for example cyclopentyl, cyclohexyl, cycloheptyl, methylcyclopentyl or cyclooctyl.

If $X^-$ is a monovalent radical of a saturated, unsaturated or aromatic carboxylic acid, it is, for example, an acetyl, caproyl, stearoyl, acryloyl, methacryloyl, benzoyl or β-(3,5-di-tert-butyl-4-hydroxyphenyl)propionyl radical.

If $X^-$ is a divalent radical of a dicarboxylic acid, it is, for example, a malonyl, succinyl, glutaryl, adipoyl, suberoyl, sebacoyl, maleoyl, itaconyl, phthaloyl, dibutylmalonyl, dibenzylmalonyl, butyl(3,5-di-tert-butyl-4-hydroxybenzyl)malonyl or bicycloheptenedicarbonyl radical.

If $X^-$ is a trivalent radical of a tricarboxylic acid, it is, for example, a trimellitoyl, citryl or nitrilotriacetyl radical.

Heteroaryl is for example pyryl, thiophenyl, furyl, pyridyl or pyrimidyl.

When $R_5$, $R_6$ and $R_7$ form a monocyclic or polycyclic heterocyclic ring, the resulting cation is for example a pyridinium, quinolinium, isoquinolinium, imidazolium or thiazolium cation.

In one embodiment of the instant invention in formula I or II —$L_1(Q^+X^-)$, —$L_2(Q^+X^-)$, and —$L_3(Q^+X^-)$, are a group

wherein $K_1$ and $K_2$ are hydrogen, $C_1$-$C_{18}$alkyl, $C_5$-$C_{12}$cycloalkyl, phenyl or $C_7$-$C_9$phenylalkyl and $K_3$ is a group

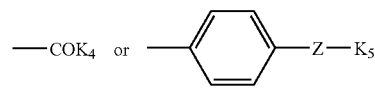

where $K_4$ is —Y—[($CH_2$—$CH_2$)—($CH_2$)$_s$—$N^+R_5R_6X^-$]$_t$—$CH_2$—$CH_2$—($CH_2$)$_s$—$N^+R_5R_6R_7X^-$ or —Y—$CH_2$—CHOH—$CH_2$—$N^+R_5R_6X^-$—{[($CH_2$—$CH_2$)—($CH_2$)$_s$—$N^+X^-R_5R_6$]$_t$—$CH_2$—$CH_2$—($CH_2$)$_s$—$N^+R_5R_6R_7X^-$}$_u$, where s is a number 0-8, t is a number 0-4 and u is 0 or 1 and Y is —O— or —$NR_9$; or $K_4$ is a group

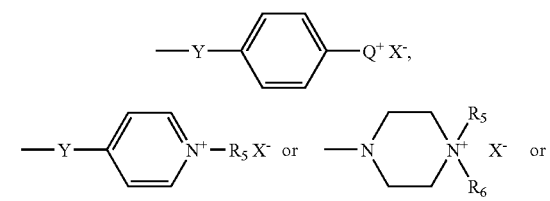

Z is —C(O)— or a direct bond, if Z is —C(O)—, $K_5$ has the same meaning as $K_4$, if Z is a direct bond, $K_5$ is Y—$CH_2$—CHOH—$CH_2$—$N^+R_5R_6X^-$—{[($CH_2$—$CH_2$)—($CH_2$)$_s$—$N^+R_5R_6X^-$]$_t$—$CH_2$—$CH_2$—($CH_2$)$_s$—$N^+R_5R_6R_7X^-$}$_u$, $Q^+X^-$, —$CH_2Q^+X^-$ or $CHCH_3Q^+X^-$;

and Y is —O— or —$NR_9$ or a direct bond;

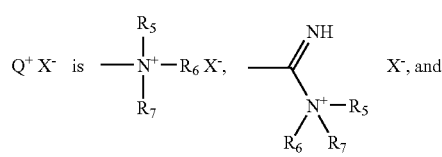

the other substituents are as defined above.

Preferably the compounds are of formulae Ia, Ib, Ic, Id or Ie

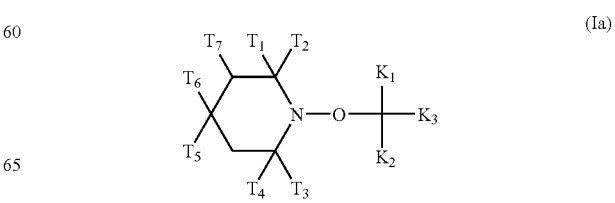

(Ia)

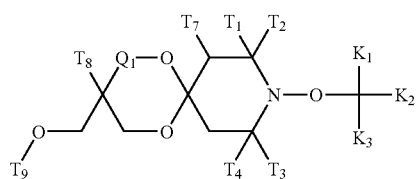
(Ib)

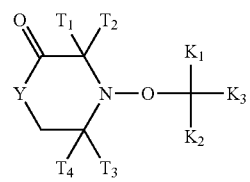
(Ic)

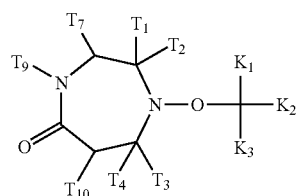
(Id)

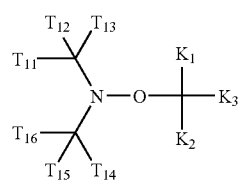
(Ie)

wherein $Q_1$ is a direct bond or a —$CH_2$— group;

if $Q_1$ is a direct bond, $T_8$ is hydrogen, if $Q_1$ is —$CH_2$—, $T_8$ is methyl or ethyl;

$T_1, T_2, T_3$ and $T_4$ are independently methyl or ethyl with the proviso that at least one is ethyl;

$T_7$ and $T_{10}$ are independently hydrogen or methyl;

$T_5$ and $T_6$ are hydrogen or $T_5$ and $T_6$ together are a group =O, =NOH, =NO—$T_9$ or $T_5$ is hydrogen and $T_6$ is —O—$T_9$ or —$NR_9$—$T_9$ where $T_9$ is hydrogen, $R_9$ or —C(O)—$R_9$, where $R_9$ is hydrogen, $C_1$-$C_{18}$alkyl, $C_3$-$C_{18}$alkenyl, $C_3$-$C_{18}$alkinyl, phenyl, $C_7$-$C_9$phenylalkyl, which may be unsubstituted or substituted by one or more hydroxy, halogen or $C_1$-$C_4$alkoxy groups;

$T_{11}, T_{12}, T_{13}, T_{14}, T_{15}$ and $T_{16}$ independently are $C_1$-$C_{18}$alkyl, $C_3$-$C_{18}$alkenyl, $C_3$-$C_{18}$alkinyl, $C_5$-$C_{12}$cycloalkyl, phenyl or $C_7$-$C_9$phenylalkyl; or $T_{11}$ is hydrogen and $T_{12}$ is a group —$P(O)(OC_2H_5)_2$ and the others are as defined above;

or $T_{11}$ and $T_{14}$ are a group —$CH_2$—O-$T_9$ and the others are as defined above; or $T_{16}$ is a group —C(O)—Y—$R_5$ and the others are as defined above; or $T_{11}, T_{12}$ and $T_{13}$ are a group —$CH_2OH$;

—$L_3(Q^+X^-)$, is a group

wherein $K_1$ and $K_2$ are hydrogen, $C_5$-$C_{12}$cycloalkyl, phenyl or $C_7$-$C_9$phenylalkyl and $K_3$ is a group

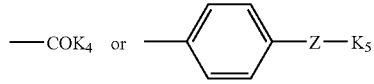

where $K_4$ is Y—[($CH_2$—$CH_2$)—($CH_2$)$_s$—$N^+R_5R_6X^-$]$_t$—$CH_2$—$CH_2$—($CH_2$)$_s$—$N^+R_5R_6R_7X^-$ or —Y—$CH_2$—CHOH—$CH_2$—$N^+R_5R_6X^-$—{[($CH_2$—$CH_2$)—($CH_2$)$_s$—$N_+X^-R_5$ $R_6$]$_t$—$CH_2$—$CH_2$—($CH_2$)$_s$—$N^+R_5R_6R_7X^-$}$_u$, where s and t is a number 0-4 and u is 0 or 1; or $K_4$ is a group

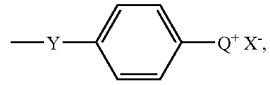

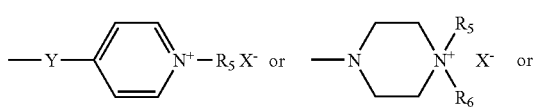

Z is —C(O)— or a direct bond, if Z is —C(O)— $K_5$ has the meaning of $K_4$, if Z is a direct bond, $K_5$ is O—$CH_2$—CHOH—$CH_2$—$N^+$ $R_5R_6X^-$—{—[($CH_2$—$CH_2$)—($CH_2$)$_s$—$N^+R_5R_6X^-$]$_t$—$CH_2$—$CH_2$—($CH_2$)$_s$—$N^+R_5R_6R_7X^-$}$_u$, $Q^+X^-$, —$CH_2Q^+X^-$ or —$CHCH_3Q^+X^-$;

Y is —O— or —$NR_9$;

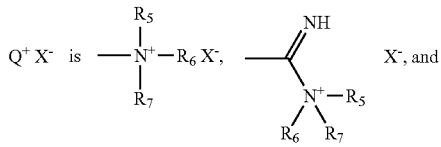

$X^-$ and the other substituents are as defined above.

In another preferred embodiment of the invention the compounds are of formula IIa, IIb, IIc, IId or IIe

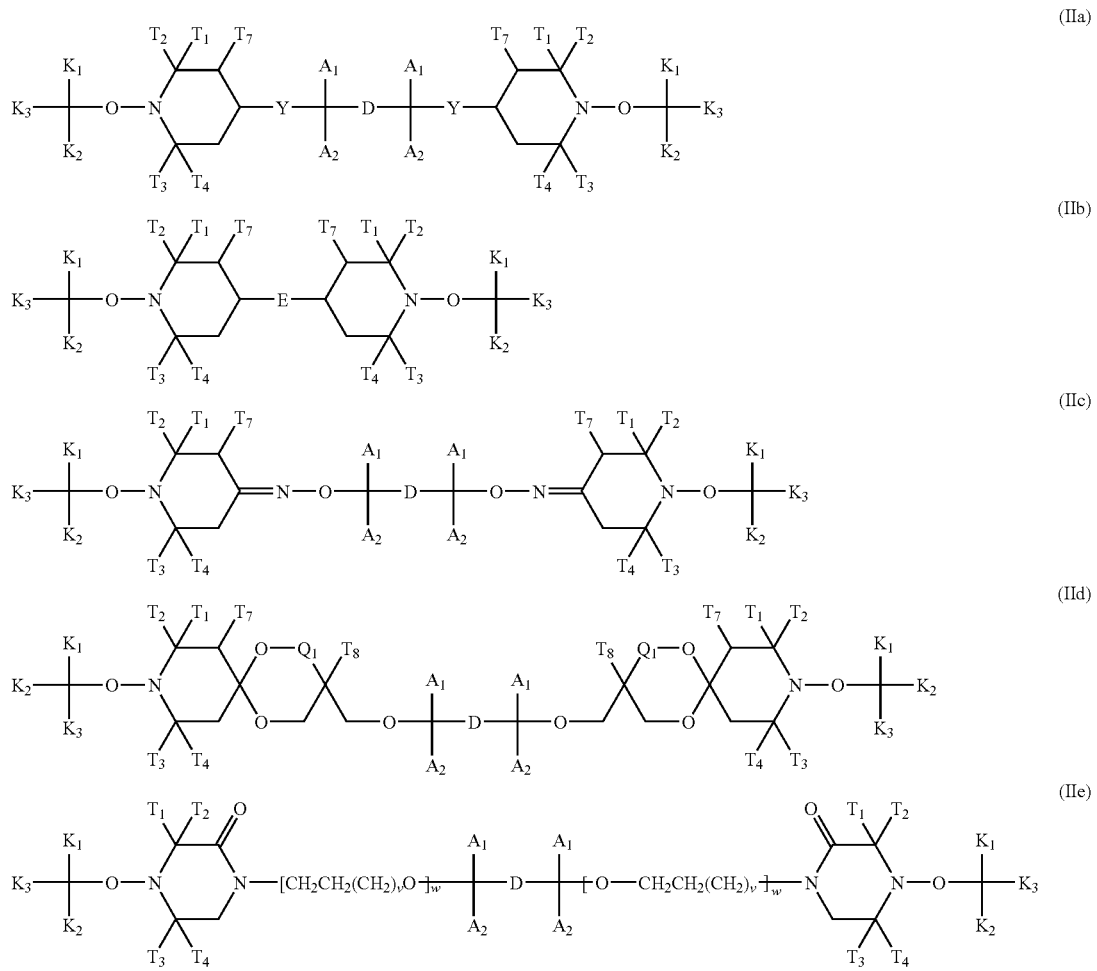

wherein $A_1$ and $A_2$ are independently hydrogen or together with the carbon atom to which they are bonded form a carbonyl group, —C(O)—;

D is a direct bond or $C_1$-$C_{12}$alkylene, $C_1$-$C_{12}$alkylene which is interrupted by one or more O, S, or $NR_9$ atoms, $C_5$-$C_{12}$cycloalkylene or phenylene;

E is a group —$NR_9$—$(CH_2)_k$—$NR_9$— where x is a number from 2 to 12 or a group

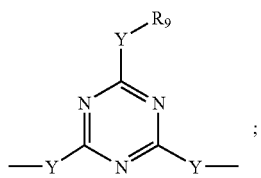

v is a number from 0 to 10 and w is 0 or 1;

$Q_1$ is a direct bond or a —$CH_2$— group;

if $Q_1$ is a direct bond, $T_8$ is hydrogen, if $Q_1$ is —$CH_2$—, $T_8$ is hydrogen, methyl or ethyl;

Y is —O— or —$NR_9$;

$T_1$, $T_2$, $T_3$ and $T_4$ are independently methyl or ethyl with the proviso that at least one is ethyl;

$T_7$ is hydrogen or methyl;

—$L_3(Q^+X^-)$, is a group

wherein $K_1$ and $K_2$ are hydrogen, $C_5$-$C_{12}$cycloalkyl, phenyl or $C_7$-$C_9$phenylalkyl and $K_3$ is a group

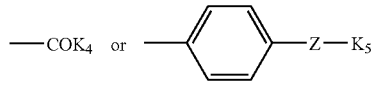

where $K_4$ is $Y-[(CH_2-CH_2)-(CH_2)_s-N^+R_5R_6X^-]_t-CH_2-CH_2-(CH_2)_s-N^+R_5R_6R_7X^-$ or $-Y-CH_2-CHOH-CH_2-N^+R_5R_6X^--\{[(CH_2-CH_2)-(CH_2)_s-N^+R_5R_6X^-]_t-CH_2-CH_2-(CH_2)_s-N^+R_5R_6R_7X^-\}_u$, where s and t is a number 0-4 and u is 0 or 1; or $K_4$ is a group

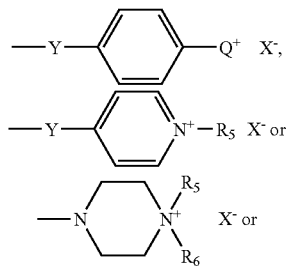

Z is —C(O)— or a direct bond, if Z is —C(O)— $K_5$ has the meaning of $K_4$, if Z is a direct bond, $K_5$ is $O-CH_2-CHOH-CH_2-N^+R_5R_6X^--\{[(CH_2-CH_2)-(CH_2)_s-N^+R_5R_6X^-]_t-CH_2-CH_2-(CH_2)_s-N^+R_5R_6R_7X^-\}_u$, $Q^+X^-$, $-CH_2Q^+X^-$ or $-CHCH_3Q^+X^-$;

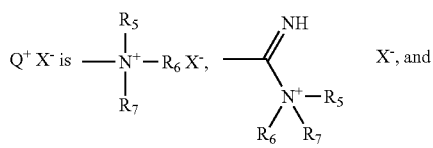

$X^-$ and the other substituents are as defined above.

Also preferred are the compounds of formula IIIa, IIIb, IIIc, IIId or IIIe

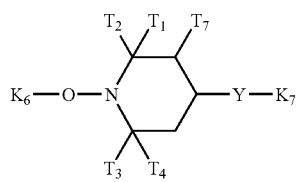
(IIIa)

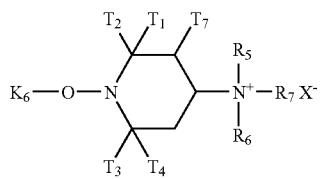
(IIIb)

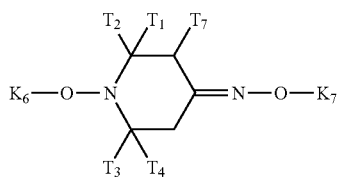
(IIIc)

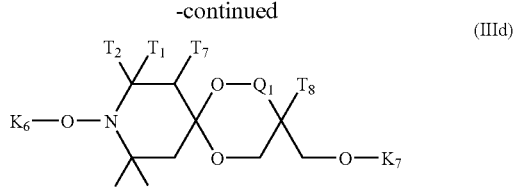
(IIId)

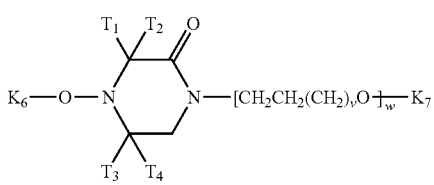
(IIIe)

$T_1$, $T_2$, $T_3$ and $T_4$ are independently methyl or ethyl with the proviso that at least one is ethyl;

$T_7$ is hydrogen or methyl;

Y is O or $NR_9$;

$Q_1$ is a direct bond or a —CH group;

if $Q_1$ is a direct bond, $T_8$ is hydrogen, if $Q_1$ is —$CH_2$—, $T_8$ is methyl or ethyl;

v is a number from 0 to 10 and w is 0 or 1;

$K_7$ is a group $-CH_2-CHOH-CH_2-N^+R_5R_6X^--\{[(CH_2-CH_2)-(CH_2)_s-N^+R_5R_6X^-]_t-CH_2-CH_2-(CH_2)_s-N^+R_5R_6R_7X^-\}_u$, where s and t is a number 0-4 and u is 0 or 1; or a group $-D_1-Q^+X^-$ where $D_1$ is $C_1$-$C_{12}$alkylene, $C_1$-$C_{12}$alkylene which is interrupted by one or more O, S, or $NR_9$ atoms, $C_5$-$C_{12}$cycloalkylene or phenylene;

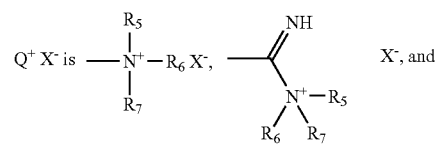

$K_6$ is selected from the group consisting of

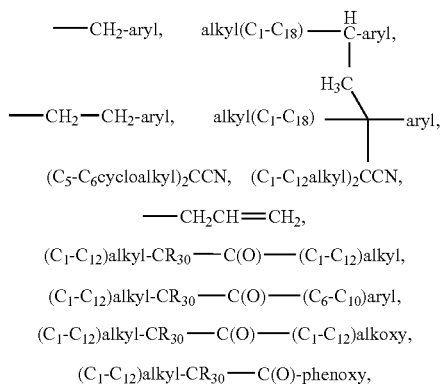

-continued (C$_1$-C$_{12}$)alkyl-CR$_{30}$—C(O)—N-di(C$_1$-C$_{12}$)alkyl, (C$_1$-C$_{12}$)alkyl-CR$_{30}$—CO—NH(C$_1$-C$_{12}$)alkyl, (C$_1$-C$_{12}$)alkyl-CR$_{30}$—CO—NH$_2$,

—CH$_2$CH=CH—CH$_3$, —CH$_2$—C(CH$_3$)=CH$_2$,

—CH$_2$—CH=CH-phenyl, —CH$_2$—C≡CH, 3-cyclohexenyl, 3-cyclopentenyl,

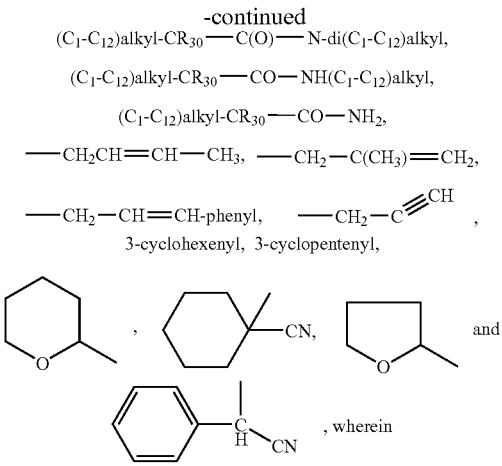, wherein

R$_{30}$ is hydrogen or C$_1$-C$_{12}$alkyl;

the alkyl groups are unsubstituted or substituted with one or more —OH, —COOH or —C(O)R$_{30}$ groups; and the aryl groups are phenyl or naphthyl which are unsubstituted or substituted with C$_1$-C$_{12}$alkyl, halogen, C$_1$-C$_{12}$alkoxy, C$_1$-C$_{12}$alkylcarbonyl, glycidyloxy, OH, —COOH or —COO(C$_1$-C$_{12}$)alkyl and X$^-$ and the other substituents are as defined above.

Particularly suitable are the compounds according to formula IVa

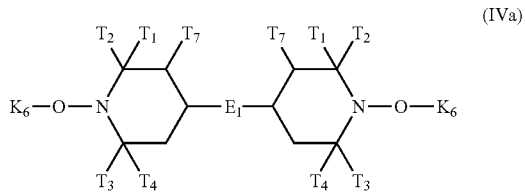 (IVa)

wherein

T$_1$, T$_2$, T$_3$ and T$_4$ are independently methyl or ethyl with the proviso that at least one is ethyl;

T$_7$ is hydrogen or methyl;

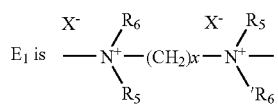

where x is a number from 2 to 12;

K$_6$ is selected from the group consisting of

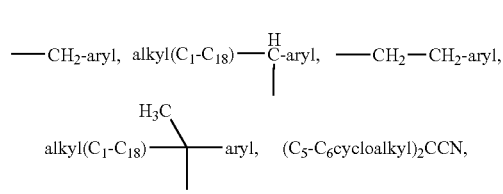

-continued (C$_1$-C$_{12}$alkyl)$_2$CCN, —CH$_2$CH=CH$_2$, (C$_1$-C$_{12}$)alkyl-CR$_{30}$—C(O)—(C$_1$-C$_{12}$)alkyl, (C$_1$-C$_{12}$)alkyl-CR$_{30}$—C(O)—(C$_6$-C$_{10}$)aryl, (C$_1$-C$_{12}$)alkyl-CR$_{20}$—C(O)—(C$_1$-C$_{12}$)alkoxy, (C$_1$-C$_{12}$)alkyl-CR$_{30}$—C(O)-phenoxy, (C$_1$-C$_{12}$)alkyl-CR$_{30}$—C(O)—N-di(C$_1$-C$_{12}$)alkyl, (C$_1$-C$_{12}$)alkyl-CR$_{30}$—CO—NH(C$_1$-C$_{12}$)alkyl, (C$_1$-C$_{12}$)alkyl-CR$_{30}$—CO—NH$_2$,

—CH$_2$CH=CH—CH$_3$, —CH$_2$—C(CH$_3$)=CH$_2$,

—CH$_2$—CH=CH-phenyl, —CH$_2$—C≡CH, 3-cyclohexenyl, 3-cyclopentenyl,

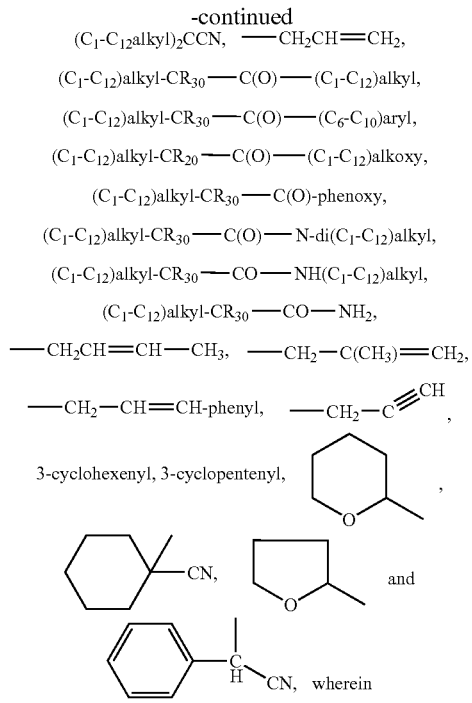, wherein

R$_{30}$ is hydrogen or C$_1$-C$_{12}$alkyl;

the alkyl groups are unsubstituted or substituted with one or more —OH, —COOH or —C(O)R$_{30}$ groups; and the aryl groups are phenyl or naphthyl which are unsubstituted or substituted with C$_1$-C$_{12}$alkyl, halogen, C$_1$-C$_{12}$alkoxy, C$_1$-C$_{12}$alkylcarbonyl, glycidyloxy, OH, —COOH or —COO(C$_1$-C$_{12}$)alkyl and X$^-$ and the other substituents are as defined above.

Preference is also given to compounds of formula Va, Vb, Vc, Vd or Ve

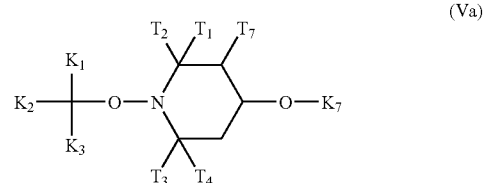 (Va)

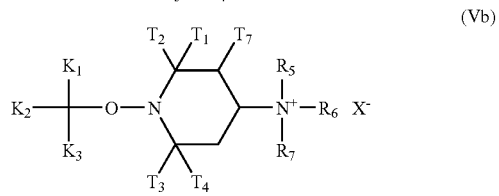 (Vb)

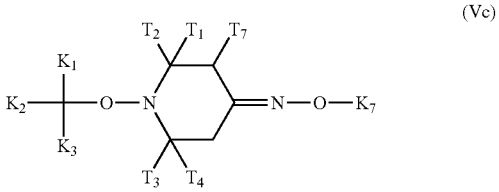 (Vc)

-continued

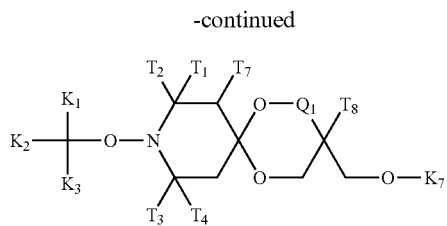
(Vd)

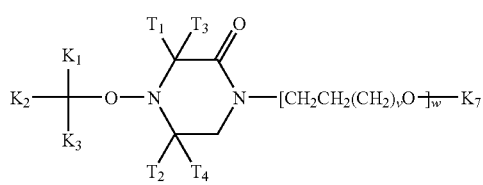
(Ve)

wherein $T_1$, $T_2$, $T_3$ and $T_4$ are independently methyl or ethyl with the proviso that at least one is ethyl;

$T_7$ is hydrogen or methyl;

$Q_1$ is a direct bond or a —$CH_2$— group;

if $Q_1$ is a direct bond, $T_8$ is hydrogen, if $Q_1$ is —$CH_2$—, $T_8$ is methyl or ethyl;

$K_1$ and $K_2$ are hydrogen, $C_5$-$C_{12}$cycloalkyl, phenyl or $C_7$-$C_9$phenylalkyl and $K_3$ is a group

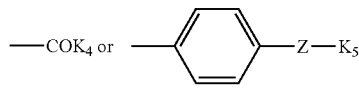

where $K_4$ is Y—[($CH_2$—$CH_2$)—($CH_2$)$_s$—$N^+R_5R_6X^-$]$_t$—$CH_2$—$CH_2$—($CH_2$)$_s$—$N^+R_5R_6R_7X^-$ or —Y—$CH_2$—CHOH—$CH_2$—$N^+R_5R_6X^-$—{[($CH_2$—$CH_2$)—($CH_2$)$_s$—$N^+R_5R_6X^-$]$_t$—$CH_2$—$CH_2$—($CH_2$)$_s$—$N^+R_5R_6R_7X^-$}$_u$, where s and t is a number 0-4 and u is 0 or 1; or $K_4$ is a group

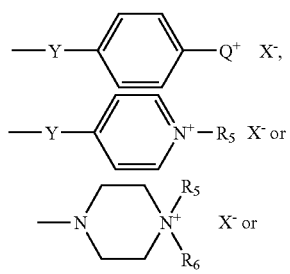

Z is —C(O)— or a direct bond, if Z is —C(O)— $K_5$ has the meaning of $K_4$, if Z is a direct bond, $K_5$ is O—$CH_2$—CHOH—$CH_2$—$N^+R_5R_6X^-$—{[($CH_2$—$CH_2$)—($CH_2$)$_s$—$N^+R_5R_6X^-$]$_t$—$CH_2$—$CH_2$—($CH_2$)$_s$—$N^+R_5R_6R_7X^-$}$_u$, $Q^+X^-$, —$CH_2Q^+X^-$ or —$CHCH_3Q^+X^-$;

$K_7$ is a group —$CH_2$—CHOH—$CH_2$—$N^+R_5R_6X^-$—{[($CH_2$—$CH_2$)—($CH_2$)$_s$—$N^+R_5R_6X^-$]$_t$—$CH_2$—$CH_2$—($CH_2$)$_s$—$N^+R_5R_6R_7X^-$}$_u$, where s and t is a number 0-4 and u is 0 or 1; or a group —$D_1$—$Q^+X^-$ where $D_1$ is $C_1$-$C_{12}$alkylene, $C_1$-$C_{12}$alkylene which is interrupted by one or more O, S, or $NR_9$ atoms, $C_5$-$C_{12}$cycloalkylene or phenylene;

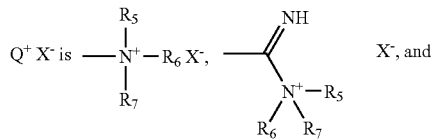

$X^-$ and the other substituents are as defined above.

Also preferred are compounds of formula VIa

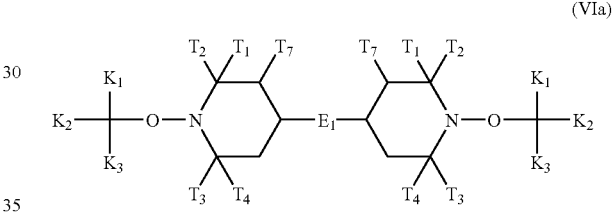
(VIa)

wherein $T_1$, $T_2$, $T_3$ and $T_4$ are independently methyl or ethyl with the proviso that at least one is ethyl;

$T_7$ is hydrogen or methyl;

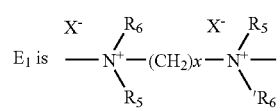

where x is a number from 2 to 12;

$K_1$ and $K_2$ are hydrogen, $C_5$-$C_{12}$cycloalkyl, phenyl or $C_7$-$C_9$phenylalkyl and $K_3$ is a group

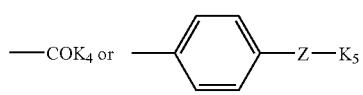

where $K_4$ is Y—[($CH_2$—$CH_2$)—($CH_2$)$_s$—$N^+R_5R_6X^-$]$_t$—$CH_2$—$CH_2$—($CH_2$)$_s$—$N^+R_5R_6R_7X^-$ or —Y—$CH_2$—CHOH—$CH_2$—$N^+R_5R_6X^-$—{[($CH_2$—$CH_2$)—($CH_2$)$_s$—$N^+R_5R_6X^-$]$_t$—$CH_2$—$CH_2$—($CH_2$)$_s$—$N^+R_5R_6R_7X^-$}$_u$, where s and t is a number 0-4 and u is 0 or 1; or $K_4$ is a group

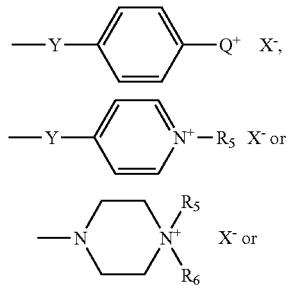

Z is —C(O)— or a direct bond, if Z is —C(O)— $K_5$ has the meaning of $K_4$, if Z is a direct bond, $K_5$ is O—CH$_2$—CHOH—CH$_2$—N$^+$R$_5$R$_6$X$^-$—{[(CH$_2$—CH$_2$)—(CH$_2$)$_s$—N$^+$R$_5$R$_6$X$^-$]$_t$—CH$_2$—CH$_2$—(CH$_2$)$_s$—N$^+$R$_5$R$_6$R$_7$X$^-$}$_u$, Q$^+$X$^-$, —CH$_2$Q$^+$X$^-$ or —CHCH$_3$Q$^+$X$^-$ and X$^-$ and the other substituents are as defined above.

Of particular interest are compounds of formula Ia1, Ib1, Ic1, Id1 or Ie1

(Ia1)

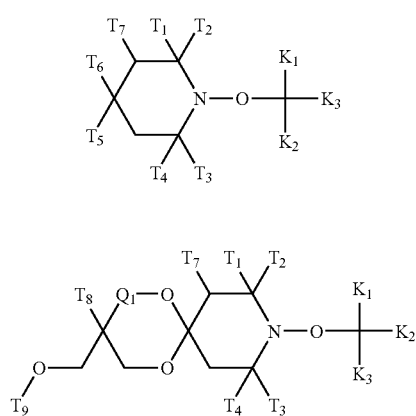

(Ib1)

(Ic1)

(Id1)

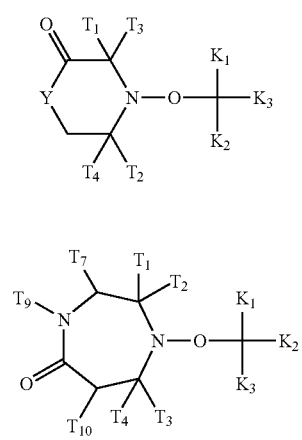

(Ie1)

wherein $Q_1$ is a direct bond or CH$_2$;

$T_1$, $T_3$ are ethyl and $T_2$, $T_4$ are methyl;

$T_7$ is methyl or H;

if $Q_1$ is a direct bond, $T_8$ is H;

if $Q_1$ is CH$_2$, $T_8$ is methyl or ethyl;

$T_{10}$ is H if $T_7$ is methyl or $T_{10}$ is methyl if $T_7$ is H;

$T_{11}$, $T_{12}$, $T_{13}$, $T_{14}$, $T_{15}$ and $T_{16}$ are independently methyl or ethyl; or $T_{11}$ is H, $T_{12}$ is isopropyl, $T_{13}$ is phenyl and $T_{14}$, $T_{15}$, $T_{16}$ are methyl; or $T_{11}$ is H, $T_{12}$ is —P(=O)(OC$_2$H$_5$)$_2$, $T_{13}$ is t-butyl and $T_{14}$, $T_{15}$, $T_{16}$ are methyl; or $T_{11}$ and $T_{14}$ are —CH$_2$O-$T_9$ and $T_{12}$, $T_{15}$ are methyl or phenyl and $T_{13}$, $T_{16}$ are methyl or ethyl; or $T_{11}$, $T_{12}$, $T_{13}$, $T_{14}$, $T_{15}$ are methyl and $T_{16}$ is a group —CO—O—$R_9$ or CON($R_9$)$_2$; or $T_{11}$, $T_{12}$ and $T_{13}$ are —CH$_2$OH, $T_{14}$ is H, $T_{15}$ is isopropyl and $T_{16}$ phenyl;

$T_9$ is hydrogen, $R_9$ or —C(O)—$R_9$, where $R_9$ is hydrogen, C$_1$-C$_{18}$alkyl, C$_3$-C$_{18}$alkenyl, C$_3$-C$_{18}$alkinyl, phenyl, C$_7$-C$_9$phenylalkyl;

$K_1$ is H, $K_2$ is methyl or ethyl and $K_3$ is a group

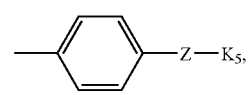

$K_4$ is —Y—CH$_2$—CH$_2$—(CH$_2$)$_r$—N$^+$X$^-$R$_5$R$_6$R$_7$ or; —Y—CH$_2$—CHOH—CH$_2$—N—CH$_2$—CH$_2$—(CH$_2$)$_s$—N$^+$X$^-$R$_5$R$_6$R$_7$ where Y is O or NR$_9$ and s is a number from 0 to 2;

if $K_3$ is

Z is —CO— or a direct bond;

if Z is —CO—, $K_5$ has the same meaning as $K_4$;

if Z is a direct bond, $K_5$ is a group —O—CH$_2$—CHOH—CH$_2$—N—CH$_2$—CH$_2$—(CH$_2$)$_s$—N$^+$X$^5$R$_5$R$_6$R$_7$ or —CH$_2$N$^+$R$_5$R$_6$R$_7$X$^-$ and X$^-$ and the other substituents are as defined above.

Also of particular interest are compounds of formula IIa1, IIb1, IIc1 or IId1

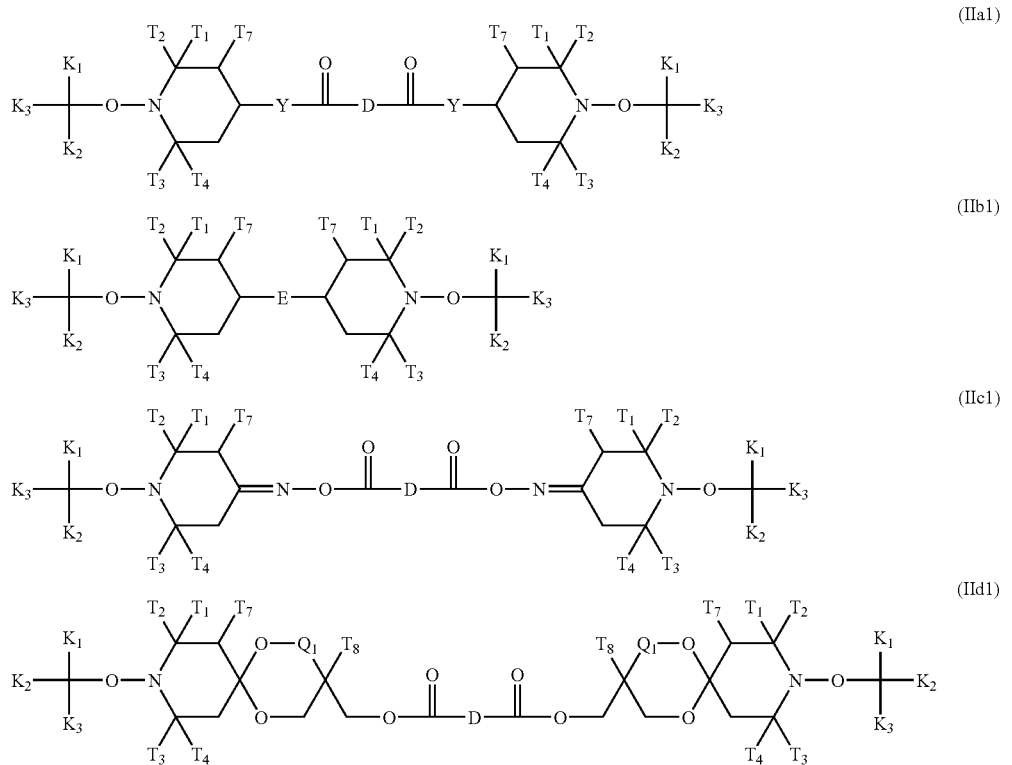

wherein $Q_1$ is a direct bond or $CH_2$;

$T_1$, $T_3$ are ethyl and $T_2$, $T_4$ and $T_7$ are methyl;

if $Q_1$ is a direct bond, $T_8$ is H;

if $Q_1$ is $CH_2$, $T_8$ is methyl or ethyl;

D is a direct bond, $C_1$-$C_{12}$alkylene or phenylene;

E is —$NR_5$—$(CH_2)_x$—$NR_5$— where x is 2 to 12 or a group

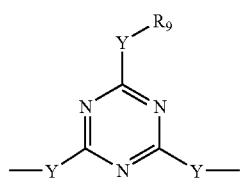

wherein Y is =$NR_9$ $K_1$ is H, $K_2$ is methyl or ethyl and $K_3$ is a group

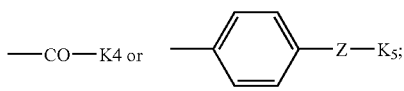

$K_4$ is —Y—$CH_2$—$CH_2$—$(CH_2)_s$—$N^+X^-R_5R_6R_7$ or; —Y—$CH_2$—CHOH—$CH_2$—N—$CH_2$—$CH_2$—$(CH_2)_s$—$N^+X^-R_5R_6R_7$ where Y is O or $NR_9$ and s is a number from 0 to 2;

if $K_3$ is

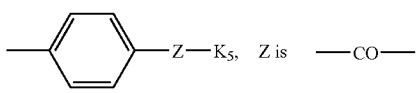

or a direct bond;

if Z is —CO— $K_5$ has the same meaning as $K_4$;

if Z is a direct bond $K_5$ is a group —O—$CH_2$—CHOH—$CH_2$—N—$CH_2$—$CH_2$—$(CH_2)_s$—$N^+X^-R_5R_6R_7$ or —$CH_2N^+R_5R_6R_7X^-$; and $X^-$ and the other substituents are as defined above.

The precursors of the above compounds can be prepared according to known methods.

The preparation of open chain alkoxyamines is for example described in WO 99/03894 or in WO 00/07981. Alkoxyamines based on tetraalkyl piperidine are for example described in GB 2 335 1290 or in GB 2 361 235. Further heterocyclic alkoxyamines are described in GB 2 342 649.

A very suitable, but not the only possible, method for the introduction of the cationic moiety into the molecule of the alkoxyamine consists of first preparing the suitable precursor alkoxyamine which is then quarternised. Examples of such alkoxyamines are given in the examples in Table 1. The non cationic precursors can be prepared by a variety of methods described in the cited patents using the suitable building blocks bearing the appropriate nucleophilic groups capable of quarternisation. Few examples of such groups are primary, secondary or tertiary amine group, pyridyl, quinolyl, isoquinolyl, imidazolyl, thiazolyl groups, trialkyl or triaryl or alkylarylphosphine groups or a thioether group. These can be quarternised by a variety of electrophilic reagents, for example alkyl halides, alkyl sulfonates, alkyl carbonates, trialkyloxonium salts, epoxides or others. A special case is the formation of the cationic moiety by protonation of the cited nucleophilic groups by their protonation with acids. A given specific anion of the cationic alkoxyamine can be exchanged against a different one using for example ion exchangers or well known ion metathesis.

A further aspect of the invention is a process for preparing a monomer/polymer clay nanocomposite dispersion comprising the steps of
  A) providing a first aqueous dispersion of a natural or synthetic clay which can be partially intercalated and/or exfoliated and wherein said clay has an exchangeable cation;
    adding a compound according to claim 1 to said dispersion and exchanging said cation at least partially;
  B) adding to said dispersion at least one ethylenically unsaturated monomer and polymerizing at least a portion of said ethylenically unsaturated monomer.

Clay minerals are typically comprised of hydrated aluminum silicates that are fine-grained and have a platy habit. The crystalline structure of a typical clay mineral is a multi-layered structure comprised of combinations of layers of $SiO_4$ tetrahedra that are joined to layers of $AlO(OH)_2$ octahedra. A so called "gallery" is formed which describes the defined interlayer spaces of the layered clay minerals. Depending on the clay mineral the gallery may contain water and/or other constituents such as potassium, sodium or calcium cations. Clay minerals vary based upon the combination their constituent layers and cations. Isomorphic substitution of the cations of clay mineral, such as $Al^{3+}$ or $Fe^{3+}$ substituting for the $Si^{4+}$ ions in the tetrahedral network, or $Al^{3+}$, $Mg^{2+}$ or $Fe^{2+}$ substituting for other cations in the octahedral network, typically occurs and may impart a net negative charge on the clay structure. Natural occurring elements within the gallery of the clay, such as water molecules or sodium or potassium cations, are attracted to the surface of the clay layers due to this net charge.

Nanocomposites are compositions in which at least one of its constituents has one or more dimensions, such as length, width or thickness in the nanometer size range. The term nanocomposite, as used herein, denotes the state of matter wherein polymer molecules exist among at least partially exfoliated clay layers.

The term "intercalated nanocomposite", as used herein describes a nanocomposite that contains a regular insertion between the clay layers.

The term "exfoliated nanocomposite" as used herein describes a nanocomposite wherein the 1 nm thick layers of clay are dispersed in the matrix (oligomer/polymer) forming a composite structure on the nano/micro scale.

The clay minerals are items of commerce and are for example supplied by Süd-Chemie Inc., Germany.

Preferably the ethylenically unsaturated monomer or oligomer is selected from the group consisting of ethylene, propylene, n-butylene, i-butylene, styrene, substituted styrene, conjugated dienes, acrolein, vinyl acetate, vinylpyrrolidone, vinylimidazole, maleic anhydride, (alkyl)acrylic acid anhydrides, (alkyl)acrylic acid salts, (alkyl)acrylic esters, (meth)acrylonitriles, (alkyl)acrylamides, vinyl halides or vinylidene halides.

Particularly the ethylenically unsaturated monomers are ethylene, propylene, n-butylene, i-butylene, isoprene, 1,3-butadiene, $\alpha$-$C_5$-$C_{18}$alkene, styrene, $\alpha$-methyl styrene, p-methyl styrene or a compound of formula $CH_2$=$C(R_a)$—$(C=Z)$-$R_b$, wherein $R_a$ is hydrogen or $C_1$-$C_4$alkyl, $R_b$ is $NH_2$, $O^-(Me^+)$, glycidyl, unsubstituted $C_1$-$C_{18}$alkoxy, $C_2$-$C_{100}$alkoxy interrupted by at least one N and/or O atom, or hydroxy-substituted $C_1$-$C_{19}$alkoxy, unsubstituted $C_1$-$C_{18}$alkylamino, di($C_1$-$C_{18}$alkyl)amino, hydroxy-substituted $C_1$-$C_{18}$alkylamino or hydroxy-substituted di($C_1$-$C_{18}$alkyl)amino, O—$CH_2$—$CH_2$—$N(CH_3)_2$ or —O—$CH_2$—$CH_2$—$N^+H(CH_3)_2 An^-$;

$An^-$ is a anion of a monovalent organic or inorganic acid;

Me is a monovalent metal atom or the ammonium ion.

Z is oxygen or sulfur.

Examples for $R_b$ as $C_2$-$C_{100}$alkoxy interrupted by at least one O atom are of formula

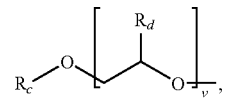

wherein $R_c$ is $C_1$-$C_{25}$alkyl, phenyl or phenyl substituted by $C_1$-$C_{18}$alkyl, $R_d$ is hydrogen or methyl and v is a number from 1 to 50. These monomers are for example derived from non ionic surfactants by acrylation of the corresponding alkoxylated alcohols or phenols. The repeating units may be derived from ethylene oxide, propylene oxide or mixtures of both.

Further examples of suitable acrylate or methacrylate monomers are given below.

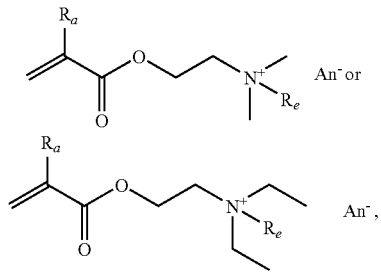

wherein $An^-$ and $R_a$ have the meaning as defined above and $R_e$ is methyl or benzyl. $An^-$ is preferably $Cl^-$, $Br^-$ or $^-O_3S$—$CH_3$.

Further acrylate monomers are

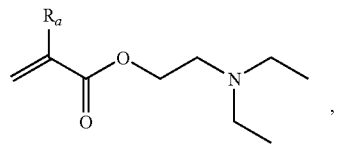

-continued

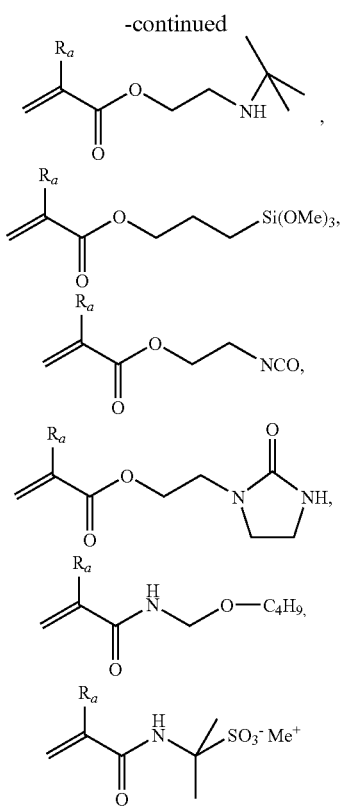

Examples for suitable monomers other than acrylates are

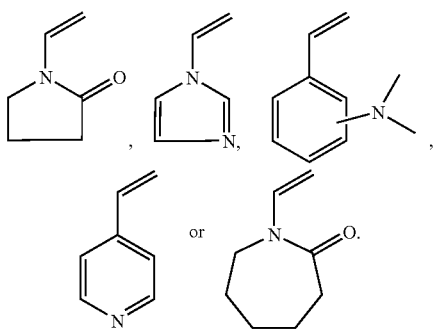

Preferably $R_a$ is hydrogen or methyl, $R_b$ is $NH_2$, glycidyl, unsubstituted or with hydroxy substituted $C_1$-$C_4$alkoxy, unsubstituted $C_1$-$C_4$alkylamino, di($C_1$-$C_4$alkyl)amino, hydroxy-substituted $C_1$-$C_4$alkylamino or hydroxy-substituted di($C_1$-$C_4$alkyl)amino; and Z is oxygen.

Also suitable ethylenically unsaturated monomers are styrene, methylacrylate, ethylacrylate, butylacrylate, isobutylacrylate, tert. butylacrylate, hydroxyethylacrylate, hydroxypropylacrylate, dimethylaminoethylacrylate, glycidylacrylates, methyl(meth)acrylate, ethyl(meth)acrylate, butyl(meth)acrylate, hydroxyethyl(meth)acrylate, hydroxypropyl(meth)acrylate, dimethylaminoethyl(meth)acrylate, glycidyl(meth)acrylates, acrylonitrile, acrylamide, methacrylamide or dimethylaminopropyl-methacrylamide.

Preferred is a process wherein the ethylenically unsaturated monomer is selected from the group consisting of $C_1$-$C_{18}$ alkyl methacrylate, $C_1$-$C_{18}$ alkyl acrylate, 2-ethylhexyl (meth)acrylate, isobornyl(meth)acrylate, lauryl(meth)acrylate, allyl(meth)acrylate, stearyl (meth)acrylate, acrylic acid, itaconic acid, methacrylic acid, butadiene, vinyl acetate, vinyl versa tate, styrene, hydroxyethyl(meth)acrylate, hydroxypropyl(meth)acrylate, vinyl aromatic monomers, divinylbenzene, divinylpyridine, divinyltoluene, diallyl phthalate, ethylene glycol di(meth)acrylate, butylene glycol di(meth)acrylate, divinylxylene, divinylethylbenzene, divinylsulfone, divinylketone, divinylsulfide, diallyl maleate, diallyl fumarate, diallyl succinate, diallyl carbonate, diallyl malonate, diallyl oxalate, diallyl adipate, diallyl sebacate, divinyl sebacate, diallyl tartrate, diallyl silicate, triallyl tricarballylate, triallyl aconitate, triallyl citrate, triallyl phosphate, N,N-methylene dimethacrylamide, N,N-methylene dimethacrylamide, N,N-ethylenediacrylamide, trivinylbenzene, and the polyvinyl ethers of glycol, glycerol, pentaerythritol, resorcinol, monothio and dithio derivatives of glycols, and combinations thereof.

Special preference is given to a process wherein an acid containing unsaturated monomer is added, which is selected from the group consisting of methacrylic anhydride, maleic anhydride, itaconic anhydride, acrylic acid, methacrylic acid, itaconic acid, maleic acid, fumaric acid, acryloxypropionic acid, (meth)acryloxypropionic acid, styrene sulfonic acid, ethylmethacrylate-2-sulphonic acid, 2-acrylamido-2-methylpropane, sulphonic acid; phosphoethylmethacrylate; the corresponding salts of the acid containing monomer; and combinations thereof.

In one embodiment of the invention the process is carried out wherein the water phase of step A) is at least partially removed before performing step B).

It is also possible that in step B) an organic solvent is additionally added.

Preferred is a process wherein the polymerization is carried out by applying heat, at a temperature of from 60° C. to 160° C.

Preferred is a process wherein the compound of formula I or II is added in an amount of from 1% to 100% by weight, based on the weight of the clay.

Preferably the weight ratio between the ethylenically unsaturated monomer added in step B) and the clay of step A) which is at least partially intercalated with a compound of formula I or II is from 500:1 to 1:5.

In a specific embodiment of the invention the process is carried out wherein a further cationic compound selected from the group of cationic surfactants is added in step A).

Typical surfactants are amino acids or alkylammonium ions.

The amino acid surfactants transfer a proton from the COOH group to the $NH_2$ group forming a $NH_3^+$ group which can exchange with a cation of the clay mineral.

For example the alkylammonium ion is $CH_3$—$(CH_2)_n$—$NH_3^+$ where n is from 1 to 18. It is believed that the alkylammonium cations readily exchange with the naturally occurring cations present inbetween the clay platelets resulting in an intercalated state.

It is also possible to repeat the process step B) with a second ethylenically unsaturated monomer which is different from the first one, leading to a block copolymer.

The clay may be a natural or synthetic clay material.

When the clay material is a synthetic one, it may be produced by gas-phase or sol-gel processes, for example $SiO_2$, [e.g. Aerosil® from Degussa; Ludox® from DuPont; Snowtex® from Nissan Chemical; Levasil® from Bayer; or Sylysia® from Fuji Silysia Chemical]; colloidal silica [e.g. Klebosol®], or organosols [e.g. Highlink® OG from Clariant].

Typical clays are natural or synthetic phyllosilicates, which may be organophilically modified montmorillonites [e.g. Nanomer® from Nanocor or Nanofil® from Suedchemie], bentonites [e.g. Cloisite® from Southern Clay Products], beidellites, hectorites, saponites, nontronites, sauconites, vermiculites, ledikites, magadiites, kenyaites or stevensites.

These materials are commercially available in its natural or partially intercalated form.

Special preference is given to a process wherein the natural or synthetic clay is selected from the group consisting of smectite, phyllosilicate, montmorillonite, saponite, beidellite, montronite, hectorite, stevensite, vermiculite, kaolinite, hallosite, synthetic phyllosilicates, and combinations thereof.

Most preferred is montmorillonite.

Further aspects of the invention are a monomer/polymer clay nanocomposite dispersion obtainable by a process as described above, a composition comprising an aqueous dispersion of a natural or synthetic clay which is partially intercalated and/or exfoliated and a compound as described above and a composition, which contains additionally an ethylenically unsaturated monomer and/or a organic solvent.

Yet another aspect of the invention is the use of a compound of formula I or II for the polymerization of ethylenically unsaturated monomers and the use of a monomer/polymer clay nanocomposite dispersion obtainable according to the process as defined above as additive in paints, coatings, inks, adhesives, reactive diluents or in thermoplastic materials.

The following examples illustrate the invention.

A) PREPARATION EXAMPLES OF THE COMPOUNDS

Example A1

{4-[1-(4-tert-butyl-2,2-diethyl-6,6-dimethyl-3-oxo-piperazine-1-yloxy)-ethyl]-benzyl}-triethyl-ammonium chloride (Compound 101, Table 1)

a) 1-tert-butyl-4-[1-(4-chloromethyl-phenyl)-ethoxy]-3,3-diethyl-5,5-dimethyl-piperazine-2-one To a solution of 13.4 g (0.052 mol) 1-tert-butyl-3,3-diethyl-5,5-dimethyl-piperazine-2-one-4-N-oxyl (prepared according to Ger. Offen. DE 19949352 A1) and 8 g (0.052 mol) 4-chloromethylstyrene in 320 ml ethanol 5 g (0.00788 mol) (S,S)-Jacobsen catalyst are added. Thereafter 9.6 ml (0.052 mol) t-butylhydroperoxide (70% in $H_2O$) are added followed by 4 g (0.010 mol) sodiumborohydride. The mixture is stirred at room temperature under argon for 20 h and subsequently evaporated under vacuum. The residue is diluted with 50 ml water and then extracted with 2×50 ml dichlormethane. The extract is dried over $MgSO_4$ and purified by chromatography on silica gel (hexane-ethylacetate 12:1). After crystallisation of the pure fraction from pentane 4.5 g of the title compound are obtained, mp. 66-68° C.

$C_{23}H_{37}ClN_2O_2$ (409.02) calculated: C, 67.54%; H, 9.12%; N, 6.85. found: C, 67.58%; H, 9.16%; N, 6.77%.

b) Quaternisation

To a solution of 20 ml triethylamine in 20 ml acetonitrile 4 g (0.0098 mol) of the product obtained under a) are added. The solution is stirred for 10 h at 60° C. and evaporated. The solid residue is suspended in 30 ml t-butyl-methyl-ether, filtrated and dried. 4.7 g of the title compound are obtained as a white powder.

$^1$H-NMR (300 MHz, $CDCl_3$): 7.57-7.49 m (2ArH), 7.41-7.38 m (2 ArH), 4.93-4.69 m (3H), 3.57-3.37 m (6H), 3.21-2.93 m (2H), 2.0-0.62 m (37H).

Example A2

4-{4-[1-(4-tert-butyl-2,2-diethyl-6,6-dimethyl-3-oxo-piperazine-1-yloxy)-ethyl]-benzoyl}-1,1-dimethyl-piperazine-1-ium iodide (Compound 102, Table 1)

a) 1-tert-butyl-3,3-diethyl-5,5-dimethyl-4-{1-[4-(4-methyl-piperazine-1-carbonyl)-phenyl]-ethoxy}-piperazine-2-one To a solution of 0.5 g (0.00124 mol) 4-[1-(4-.tert.-butyl-2,2-diethyl-6,6-dimethyl-3-oxo-piperazin-1-yloxy)-ethyl]-benzoic acid (prepared according to WO 01/02345 A2) in 10 ml dichlormethane 0.4 g (0.00248 mol) carbonyldiimidazol are added. The mixture is stirred for 30 minutes under argon at room temperature. Subsequently 0.275 ml (0.00248 mol) N-methylpiperazine is added and the solution is stirred for further 12 h. The solution is then washed 3× with 5 ml water, dried over $MgSO_4$, and evaporated. The residue is purified by chromtography on silica gel (hexane-ethylacetate 2:1) and 0.46 g of the title compound are obtained as viscous oil.

$^1$H-NMR (300 MHz, $CDCl_3$): 7.39-7.28 m (4 ArH), 4.75-4.69 m (1H), 4-0.65 m (41H).

b) Quaternisation

To a solution of 1 g (0.002 mol) of the product obtained under a) in 2 ml acetonitrile 2 ml methyliodide are added and the solution is stirred at room temperature for 1 h. After evaporation 1.2 g of the title compound are obtained as yellow powder.

$^1$H-NMR (300 MHz, DMSO-$d_6$): 7.45 s (4 ArH), 4.79-4.73 m (1H), 4.1-0.58 m (43H).

Example A3

{3-[2-(2,6-diethyl-2,3,6-trimethyl-piperidine-1-yloxy)-propionylamino]-propyl}ethyl-dimethyl-ammonium bromide (Compound 103, Table 1)

a)
2-chloro-N-(3-dimethylamino-propyl)-propionamide

To 12.25 g (0.1 mol) 2-chlorpropionic acid-methylester 10.25 g (0.1 mol) 3-dimethylamino-1-propylamine are added at such a rate, that the reaction temperature remains below 40° C. The mixture is stirred for 4 h at room temperature and subsequently evaporated at 40° C./1 mbar. Thereafter, the methanol formed in the reaction is distilled off. 18.4 g of the title compound are obtained as colorless oil.

$^1$H-NMR (300 MHz, $CDCl_3$): 8.47 bs (NH), 4.41-4.34 q (1H), 3.40-3.34 m (2H), 2.47-2.40 m (2H), 2.24 s (6H), 1.70-1.68 d (3H), 1.73-1.64 m (2H)

b) 2-(2,6-diethyl-2,3,6-trimethyl-piperidine-1-yloxy)-N-(3-dimethylamino-propyl)-propionamide To a solution of 13.85 g (0.07 mol) 2,6-Diethyl-2,3,6-trimethyl-piperidin-1-N-oxyl (prepared according to Ger. Offen. DE 2621841) in 70 ml ethylacetate 13.9 g (0.14 mol) Cu(I)-chloride are added under argon followed by 24.25 g (0.14 mol) pentamethyldiethylentriamine (PMDETA). Subsequently within 10 minutes 14.95 g (0.0735 mol) of the product obtained under a) are added dropwise. The mixture is stirred at room temperature for 12 h, followed by further addition of 3.05 g of the chloramide prepared under a), 2 g CuCl and 4.3 ml PMDETA, 20 ml ethylacetate and 10 ml DMF. The mixture is then stirred for further 96 h at room temperature. The suspension is filtered and the filter cake is washed with 100 ml ethylacetate. The filtrate is washed with 3×100 ml water, then with 2×60 ml of a 1% aqueous EDTA-disodiumsalt-solution and dried over $MgSO_4$. The residue is purified by chromatography on silica gel (hexane-ethylacetate 2:1). 7.7 g of the title compound are obtained as thick yellow oil.

$C_{20}H_{41}N_3O_2$ (355.8) found: $MH^+$=356.3 (APCI-MS).

c) Quaternisation

To a solution of 7.6 g (0.0214 mol) of the product obtained under b) in 10 ml acetonitrile 10 ml ethylbromide are added and the solution is stirred for 12 h at room temperature. After evaporation 9 g of the title compound are obtained as white powder.

For $[C_{22}H_{46}N_3O_2]^+×Br^-$=[384.64]×[79.904]. found $M^+$ (Cation)=384.6 (Infusion ESI-MS)

Example A4

{3-[2-(2,6-diethyl-4-hydroxy-2,3,6-trimethyl-piperidine-1-yloxy)-propionylamino]-propyl}-ethyl-dimethyl-ammonium bromide (Compound 104, Table 1)

a) 2-(2,6-diethyl-4-hydroxy-2,3,6-trimethyl-piperidine-1-yloxy)-.N.-(3-dimethylamino-propyl)-propionamide To a solution of 21.4 g (0.1 mol) 2,6-diethyl-4-hydroxy-2,3,6-trimethyl-piperidine-1-N-oxyl (prepared according to Ger. Offen. DE 19909767 A1) in 50 ml DMF 19.8 g (0.2 mol) Cu(I)-chloride are added under argon. Subsequently 34.7 g (0.2 mol) pentamethyldiethylentriamine (PMDETA) and 22.1 g (0.11 mol) 2-chloro-N-(3-dimethylamino-propyl)-propionamide (prepared according to example A3) are added within 20 minutes. The temperature during addition is kept below 40° C. The mixture is stirred 4 h at room temperature followed by the addition of 500 ml water and 150 ml dichlormethane. The organic phase is separated and the water phase is extracted with 2×100 ml dichlormethane. The organic phases are washed with 5×100 ml water, then with 3×60 ml 1% aqueous EDTA-Disodiumsalt-solution, dried over $MgSO_4$ evaporated. 33.55 g of the title compound are obtained as thick yellow oil.

$^1$H-NMR (300 MHz, $CDCl_3$): 7.34-7.14 bs (1H), 4.29-4.20 m (2H), 3.6-3.1 m (2H), 2.6-0.83 m (30H), 2.22 s (6H).

b) Quaternisation

To a solution of 28.35 g (0.076 mol) of the product obtained under a) in 25 ml acetonitrile 25 ml ethylbromide are added and the solution is stirred for 12 h at room temperature. After evaporation 36.5 g of the title compound are obtained as white powder.

For $[C_{22}H_{46}N_3O_3]^+×Br^-$=[400.626]×[79.904]. found $M^+$ (Kation)=400.4 (Infusion ESI-MS)

Example A5

[3-(2-{.N.-.tert.-butyl-.N.-[1-(diethoxy-phosphoryl)-2,2-dimethyl-propyl]-aminooxy}-propionylamino)-propyl]-ethyl-dimethyl-ammonium bromide (Compound 105, Table 1)

a) (1-{.tert.-butyl-[1-(3-dimethylamino-propylcarbamoyl)-ethoxy]-amino}-2,2-dimethyl-propyl)-phosphonic acid diethyl ester From 5.01 g (0.017 mol) N-(1,1-Dimethylethyl)-N-(1-diethylphosphono-2,2-dimethylpropyl)-N-oxyl (prepared according to Macromolecules (2000), 33(4), 1141-1147), 3.35 g (0.034 mol) CuCl, 5.9 g (0.034 mol) PMDETA and 3.95 g (0.0196 mol) 2-chloro-N-(3-dimethylamino-propyl)-propionamide (prepared according to example A3) in 10 ml DMF 5.6 g of the title compound are obtained as thick yellowish oil in analogy to example A4 (reaction time 19 h).

For $C_{21}H_{46}N_3O_5P$ (451.59) calculated C, 55.85%; H, 10.27%; N, 9.31%. found C, 55.09%; H, 9.91%; N, 8.86%.

b) Quaternisation

To a solution of 4.95 g (0.011 mol) of the product obtained under a) in 23 ml acetonitrile 3.3 ml ethylbromide are added and the solution is stirred for 17 h at room temperature. The suspension is evaporated, the residue is suspended in 25 ml diethylether and filtered. 5.45 g of the title compound are obtained as a white powder.

Example A6

{3-[2,6-Diethyl-2,3,6-trimethyl-1-(1-phenyl-ethoxy)-piperidine-4-ylidene-aminooxy]-propyl}ethyl-dimethyl-ammonium-bromide (Compound 106, Table 1)

a) 2,6-Diethyl-2,3,6-trimethyl-1-(1-phenyl-ethoxy)-piperidine-4-one-O-(3-dimethylamino-propyl)-oxime To a slurry of sodium hydride (4.36 g, 0.1 mol, 55% in mineral oil) in DMF (30 ml) is added dropwise the solution of 2,6-diethyl-2,3,6-trimethyl-1-(1-phenyl-ethoxy)-piperidine-4-one oxime (16.6 g, 0.05 mol, prepared as described in WO 02/100831 A1). The mixture is stirred 150 min at 25° C. and then 3-dimethylaminopropylchloride (9.48 g, 0.06 mol) is added during 1 h. The mixture is stirred at room temperature for 18 h, the DMF is then evaporated in vacuo. The residue is dissolved in ethyl acetate (100 ml), washed with water (2×25 ml), dried over $MgSO_4$ and evaporated. Chromatography on silica gel column (hexane-ethylacetate 1:1) affords 12.55 g of the title compound as a colorless oil.

MS (DEP-Cl), $C_{25}H_{43}N_3O_2$ (417.64): found 418 (100, $[M+H]^+$).

b) Quaternisation

Ethylbromide (7.5 ml) is added to a solution of 2,6-diethyl-2,3,6-trimethyl-1-(1-phenyl-ethoxy)-piperidine-4-one-O-(3-dimethylamino-propyl)-oxime (10.2 g, 0.0244 mol) in acetonitrile (12 ml). The solution is stirred 24 h at room temperature and is then evaporated. The residue is dissolved in dichloromethane, dried over $MgSO_4$ and evaporated to afford 11.5 g of the title compound as a white powder.

MS (ESI), cation $C_{27}H_{48}N_3O_2$ (446.4): found 446.9.

Example A7

{3-[2-(2,6-Diethyl-4-hydroxy-2,3,6-trimethyl-piperidine-1-yloxy)-propionyl-amino]-propyl}-ethyl-dimethyl-ammonium-bromide-terephthalate (Compound 107, Table 1)

a) Terephthalic acid bis-(2,6-diethyl-2,3,6-trimethyl-piperidine-N-oxyl-4-yl)ester Terephthaloylchloride (12.2 g, 0.06 mol) is added dropwise to a solution of 2,6-diethyl-2,3,6-trimethyl-piperidine-4-hydroxy-N-oxyl (25.72 g, 0.12 mol, prepared as described in DE 19909767 A1) in dichloromethane (80 ml) and pyridine (30 ml). The mixture is stirred 72 h, is then diluted with dichloromethane (100 ml) and water (100 ml). The organic layer is washed with water (2×50 ml), dried over MgSO4 and evaporated. The residue is chromatographed on silica gel column (500 g, hexanes-ethylacetate 4:1) to afford 31.85 g of the title compound as a thick red oil.

b) Terephthalic acid bis-{1-[1-(3-dimethylamino-propylcarbamoyl)-ethoxy]-2,6-diethyl-2,3,6-trimethyl-piperidine-4-yl}ester Terephthalic acid bis-(2,6-diethyl-2,3,6-trimethyl-piperidine-N-oxyl-4-yl) ester (16.76 g, 0.03 mol), CuCl (11.9 g, 0.12 mol), PMDETA (20.8 g, 0.12 mol) and 2-chloro-N-(3-dimethylami-no-propyl)-propionamide (13.7 g, 0.071 mol) are reacted as described in Example A3 to afford 21.1 g of the title compound as amorphous solid.

MS (APCI), $C_{48}H_{84}N_6O_8$ (873.24): found $M^+$=872.8.

c) Quaternisation

Ethylbromide (7.5 ml) is added to a solution of terephthalic acid bis-{1-[1-(3-dimethylami-no-propylcarbamoyl)-ethoxy]-2,6-diethyl-2,3,6-trimethyl-piperidine-4-yl}ester (11.0 g, 0.0125 mol) in acetonitrile (20 ml). The mixture is stirred at room temperature for 17 h and is then evaporated to afford 14.1 g of the title compound as a colorless amorphous solid.

MS (ESI), cation $C_{52}H_{94}N_6O_8$ (930.7): found 931.8.

Example A8

Ethyl-{3-[2-(4-hydroxy-2,2,6,6-tetramethyl-piperidine-1-yloxy)-propionylamino]-propyl}-dimethyl-ammonium-bromide (Compound 108, Table 1)

a) N-(3-Dimethylamino-propyl)-2-(4-hydroxy-2.2,6,6-tetramethyl-piperidine-1-yloxy)-propionamide 4-Hydroxy-TEMPO (25.84 g, 0.15 mol), CuCl (29.7 g, 0.3 mol), PMDETA (52.0 g, 0.3 mol) and 2-chloro-N-(3-dimethylamino-propyl)-propionamide (35.75 g, 0.18 mol) are reacted as described in Example A3. The final purification of the residue after the extractive workup is performed by crystallization from toluene (45 ml) and hexane (50 ml) to afford 31.13 g of the title compound as a white solid, mp. 85-88° C.

For $C_{17}H_{35}N_3O_3$ (329.49) calc %/found %: C, 61.97/61.85; H, 10.71/10.55; N, 12.75/12.61.

b) Quaternisation

Ethylbromide (9.85 ml) is added to a solution of N-(3-dimethylaminopropyl)-2-(4-hydroxy-2,2,6,6-tetramethyl-piperidine-1-yloxy)-propionamide (10.9 g, 0.033 mol) in acetonitrile (30 ml). The mixture is stirred at room temperature for 22 h and is then evaporated to afford 14.7 g of the title compound as a colorless amorphous solid.

MS (ESI) cation $C_{19}H_{40}N_3O_3$ (358.3): found 358.6.

Example A9

{3-[2-(2,6-diethyl-4-hydroxy-2,3,6-trimethyl-piperidine-1-yloxy)-2-methyl-propionylamino]-propyl}-ethyl-dimethyl-ammonium-bromide (Compound 109, Table 1)

Ethylbromide (12 ml) is added to a solution of 2-(2,6-diethyl-4-hydroxy-2,3,6-trimethyl-piperidine-1-yloxy)-N-(3-dimethylamino-propyl)-2-methyl-propionamide (20.5 g, 0.053 mol, compound 110) in acetonitrile (35 ml). The mixture is stirred for 18 h at room temperature and is then evaporated to afford 26.63 g of the title compound as a colorless solid.

MS (ESI) cation $C_{23}H_{48}N_3O_3$ (414.4): found 414.5.

Example A10

2-(2,6-Diethyl-4-hydroxy-2,3,6-trimethyl-piperidine-1-yloxy)-.N.-(3-dimethylamino-propyl)-2-methyl-propionamide (Compound 110, Table 1)

a) 2-Bromo-N-(3-dimethylamino-propyl)-2-methyl-propionamide

To a solution of 3-dimethylaminopropylamine (25 ml, 0.1 mol) in THF (50 ml) was added dropwise over 50 minutes and while keeping the temperature between 0-10° C. bromoisobutyroyl bromide (23.0 g, 0.1 mol). The mixture is stirred for another 3 h at room temperature and the THF is then evaporated in vacuo. Water (20 ml) is added to the residue and the mixture is extracted with t-butyl-methyl ether (2×30 ml) and ethylacetate (30 ml).

The combined extracts are washed with saturated NaCl solution (10 ml), dried over $MgSO_4$ and evaporated to afford 24.1 g of the title compound as a colorless oil.

$^1$H-NMR (300 MHz, $CDCl_3$): 8.51 (bs, NH), 3.39-3.34 (m, $CH_2$), 2.47-2.43 (t, $CH_2$), 2.25 (s, 2×$CH_3$), 1.94 (s, 2×$CH_3$), 1.72-1.64 (m, $CH_2$)

b) 2-(2,6-Diethyl-4-hydroxy-2,3,6-trimethyl-piperidine-1-yloxy)-N-(3-dimethylamino-propyl)-2-methyl-propionamide 2,6-diethyl-2,3,6-trimethyl-piperidine-4-hydroxy-N-oxyl (12.86 g, 0.06 mol, prepared as described in DE 19909767 A1), CuCl (11.9 g, 0.12 mol), PMDETA (20.8 g, 0.12 mol) and 2-bromo-N-(3-dimethylamino-propyl)-2-methyl-propionamide (16.5 g, 0.066 mol) are reacted as described in Example A3 to afford 23.6 g of the title compound as a white amorphous solid.

$^1$H-NMR (300 MHz, $CDCl_3$): 7.4-7.25 (bs, NH), 4.19-4.11 (m, 1H), 3.44-3.24 (m, 2H), 2.39-0.79 (m, 39H).

Example A11

Benzyl-{3-[2-(2,6-diethyl-4-hydroxy-2,3,6-trimethyl-piperidine-1-yloxy)-2-methyl-propionylamino]-propyl}-dimethyl-ammonium-chloride (Compound 111, Table 1)

Benzylchloride (0.87 g, 0.0069 mol) is added to a solution of 2-(2,6-diethyl-4-hydroxy-2,3,6-trimethyl-piperidine-1-yloxy)-N-(3-dimethylamino-propyl)-2-methyl-propionamide (2.2 g, 0.0057 mol, compound 110) in acetonitrile (3 ml). The mixture is stirred for 19 h at room temperature and is then evaporated. The residue is triturated with diethylether to remove the excess of benzylchloride, the solid is filtered off and dried to afford 3.0 g of the title compound as a colorless amorphous solid.

MS (ESI) cation $C_{28}H_{50}N_3O_3$ (476.4): found 476.4.

Example A12

Benzyl-{3-[2-(2,6-diethyl-4-hydroxy-2,3,6-trimethyl-piperidine-1-yloxy)-propionylamino]-propyl}-dimethyl-ammonium-chloride (Compound 112, Table 1)

Benzylchloride (3.8 g, 0.03 mol) is added to a solution of 2-(2,6-diethyl-4-hydroxy-2,3,6-trimethyl-piperidine-1-yloxy)-.N.-(3-dimethylamino-propyl)-propionamide (10.1 g, 0.0272 mol) in acetonitrile (15 ml). The mixture is stirred for 18 h at room temperature and is then evaporated. The residue is triturated with diethylether to remove the excess of benzylchloride, the solid is filtered off and dried to afford 13.1 g of the title compound as a colorless amorphous solid.

$^1$H-NMR (300 MHz, MeOH-d4): 7.60-7.51 (m, $C_6H_5$), 4.56 (s, $CH_2$), 4.25-4.15 (m, 2H), 3.35-3.29 (m, 4H), 3.06 (s, 6H), 2.15-0.80 (m, 29H).

Example A13

Tributyl-{3-[2-(2,6-diethyl-4-hydroxy-2,3,6-trimethyl-piperidine-1-yloxy)-propionyloxy]-propyl}-phosphonium-bromide (Compound 113, Table 1)

a) 2-Bromo-propionic acid 3-bromo-propyl ester

3-Bromopropanol (10.75 g, 0.075 mol) is added over 20 minutes to a solution of 2-bromopropionylbromide (17.9 g, 0.079 mol) in toluene (75 ml) while keeping the temperature between 15-20° C. The mixture is stirred for 6 h at room temperature and is then poured under vigorous stirring into 1M solution of $Na_2CO_3$ (80 ml). The organic layer is separated, washed with water (3×50 ml), dried over $MgSO_4$ and evaporated to afford 19.75 g of the title compound as a colorless oil.

$^1$H-NMR (300 MHz, $CDCl_3$): 4.42-4.24 (m, $CH+CH_2$), 3.55-3.47 (t, $CH_2$), 2.27-2.19 (m, $CH_2$), 1.84-1.82 (d, $CH_3$).

b) 2-(2,6-Diethyl-4-hydroxy-2,3,6-trimethyl-piperidine-1-yloxy)-propionic acid 3-bromo-propyl ester 2,6-diethyl-2,3,6-trimethyl-piperidine-4-hydroxy-N-oxyl (10.7 g, 0.05 mol, prepared as described in DE 19909767 A1), CuCl (9.9 g, 0.1 mol), PMDETA (17.3 g, 0.1 mol) and 2-bromo-propionic acid 3-bromo-propyl ester (17 g, 0.055 mol) are reacted as described in Example A3 to afford 16.4 g of the title compound as a colorless oil.

$^1$H-NMR (300 MHz, $CDCl_3$): 4.38-4.17 (m, 4H), 3.54-3.46 (m, 2H), 2.23-0.79 (m, 28H).

c) Quaternisation

Tributylphosphine (3 ml, 0.012 mol) is added to a solution of 2-(2,6-diethyl-4-hydroxy-2,3,6-trimethyl-piperidine-1-yloxy)-propionic acid 3-bromo-propyl ester (4.08 g, 0.01 mol) in acetonitrile (5 ml). The solution is stirred under argon at 60° C. for 23 h. The solvent is evaporated and the residue is triturated with diethyl ether (2×15 ml) to remove the excess of the phosphine. Drying of the oily, in ether insoluble, residue affords 6.45 g of the title compound as a thick resin.

$^1$H-NMR (300 MHz, $CDCl_3$): 4.38-4.13 (m, 4H), 2.66-2.47 (m, 8H), 2.1-0.83 (m, 49H).

The compounds are summarized in Table 1

TABLE 1

| No | Stucture |
| --- | --- |
| 101 | |
| 102 | |
| 103 | |

TABLE 1-continued
| No | Structure |
|----|-----------|
| 104 | 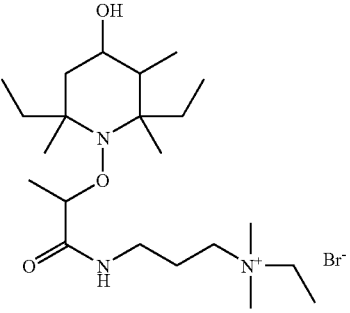 |
| 105 | 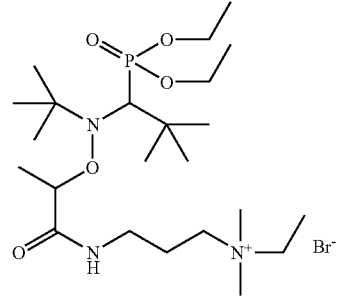 |
| 106 | 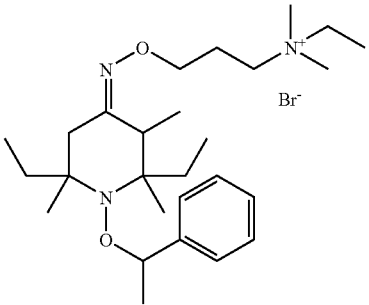 |
| 107 | 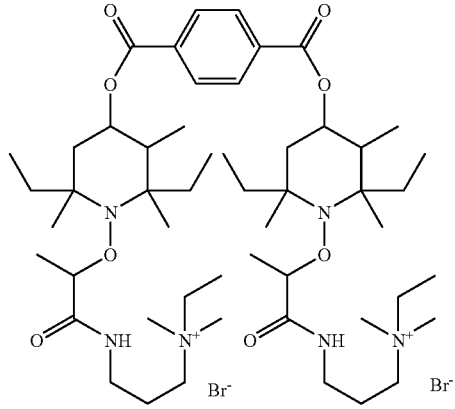 |
TABLE 1-continued
| No | Structure |
|----|-----------|
| 108 | 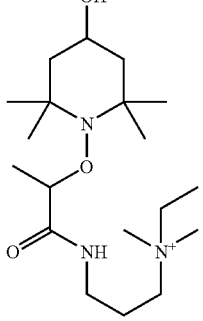 |
| 109 | 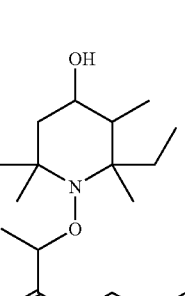 |
| 110 | 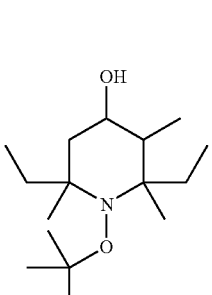 |
| 111 | 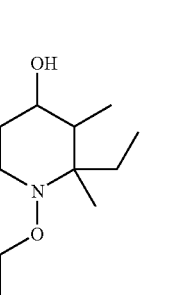 |

TABLE 1-continued

| No | Stucture |
|---|---|
| 112 | (structure: 4-hydroxy-TEMPO-derived alkoxyamine with amide linker to propyl-trimethyl-benzyl ammonium chloride) |
| 113 | (structure: 4-hydroxy-TEMPO-derived alkoxyamine with amide linker to propyl-tributyl phosphonium bromide) |

B) APPLICATION EXAMPLES PROOF OF POLYMERIZATION

Polymerization of n-butyl Acrylate with Cationic Alkoxyamines (NOR's)

The cationic NOR's are tested in pure n-butyl acrylate monomer: In a 50 ml round bottom flask with vacuum and nitrogen inlet and magnetic stirrer 10 g n-butyl acrylate (BASF, techn. quality) is mixed with 1.5 mol % of the cationic alkoxyamine (NOR), evacuated and purged with nitrogen 3 times and polymerized at 140° C. (examples B1-B4) in an oil bath for 7-20 h under good stirring. The conversion is measured by $^1$H-NMR, $M_n$ and PDI with GPC in THF, values are relative to PS-standards. The polymerization results are presented in Table 2

TABLE 2

| NOR | Time | ConversionUmsatz % ($^1$H-NMR) | $M_n$ (found) | PDI |
|---|---|---|---|---|
| Example B1 Compound 101 | 17 h | 90% | 6980 | 1.47 |
| Example B2 Compound 102 | 20 h | 78% | 5470 | 1.24 |
| Example B3 Compound 103 | 7 h | 70% | 6660 | 1.68 |
| Example B4 Compound 104 | 7 h | 60% | 5080 | 1.46 |
| Example B5 | 7 h | 42% | 3770 | 1.35 |
| Compound 106 | 120° C. 7 H 140° C. | 94% | 6600 | 1.49 |
| Example B6 Compound 107 | 22 h 140° C. | 76% | 4000 | 1.88 |
| Example B7 Compound 110 | 5 h 140° C. | 71% | 6150 | 1.21 |
| Example B8 Compound 111 | 7 h 140° C. | 65% | 6270 | 1.34 |
| Example B9 Compound 112 | 7 h 140° C. | 58% | 3680 | 2.18 |

The results presented in Table 2 clearly show that all compounds are able to initiate a controlled polymerization of n-butylacrylate.

C) APPLICATION EXAMPLES INTERCALATION OF SHEET SILICATES WITH CATIONIC NOR'S

Example C1

Intercalation of Nanofil EXM 588 (Layered Silicate of Montmorillonite-Type from Süd Chemie, Germany) with Compound 101

In a 50 ml round bottom flask 2.0 g Nanofil EXM 588 is dispersed in 30 ml of a 0.05 M solution of compound 101 in water and stirred with magnetic stirring during 24 h at R.T. After centrifugation (IEC Centra GP8 Zentrifuge, 100-180 ml glass vessels) with 2000 rpm (corresponding to ca. 850 g) during 20 min, a sample is taken of the supernatent clear solution, from which the concentration of remaining (=non intercalated) compound 101 is determined by UV-spektroscopy at λ245 nm. The intercalated quantity of compound 101 is determined to be 358 mg (=0.702 mmol) for 1 g of layered silicate.

The supernatant solution is decanted and the solid washed with water, centrifugation and decantation 3 times. This procedure is repeated with MeOH. The sedimented, washed product is subjected to a powder X-ray (λ=1.54 Angström), giving a main reflection at $2\Theta_{max.}=3.86°$, which corresponds to an interlayer distance d of 2.29 nm. Compared with the native sheet silicate ($2\Theta_{max.}=7.1°$, =>d=1.24 nm) an increase of the interlayer distance of 1.05 nm is obtained, corresponding to approximately the size of the intercalated molecule. The reflex at $2\Theta_{max.}=7.1°$ (d=1.24 nm), corresponding to the original sheet distance has almost completely disappeared.

In order to check the adsorbed quantity of intercalated compound 101, a sample is completely dried in vacuum and the weight loss determined by thermographimetric analysis (TGA): heating rate: 10° C./min, from room temperature to 600° C. The obtained weight loss of 26.3% corresponds very well to the theoretical value of 26.4%.

Examples C2-C5 are carried out in analogy to Example C1, the following cationic NOR's are intercalated into Nanofil EXM 588: The results are given in Table 3.

TABLE 3

| Example No. | NOR | Intercalated amount NOR* | Sheet distance after intercalation | Remarks |
|---|---|---|---|---|
| Example C2 | Compound 104 | 22.7 wt. % (=0.47 mmol/g) | $2\Theta_{max.} = 4.2°$, => d = 2.11 nm | ≈complete exchange |
| Example C3 | Compound 103 | 24.9 wt. % (=0.53 mmol/g) | $2\Theta_{max.} = 4.3°$, => d = 2.03 nm | ≈complete exchange |
| Example C4 | Compound 111 | 29.2 wt. % (=0.61 mmol/g) | d = 2.21 nm | ≈complete exchange |
| Example C5 | Compound 112 | 25 wt. % | d = 2.10 nm | ≈complete exchange |

*based on the total weight layered silicate + NOR compound

D) APPLICATION EXAMPLES POLYMERIZATION OF INTERCALATED SHEET SILICATES WITH CATIONIC NOR'S

Example D1

In a 50 ml round bottom flask with magnetic stirring and vacuum and nitrogen inlet 0.5 g with compound 101 intercalated Nanofil EXM588 in 9.5 g n-butyl acrylate (BASF, techn. quality) and 4.28 g 2-methoxypropyl acetate is dispersed and homogenized in an ultrasonic bath. After evacuation and purging 5 times with $N_2$, the monomer is polymerized during 9 h at 140° C. (bath temperature) under vigorous stirring. The monomer conversion, determined by $^1$H-NMR, is 85%. The dispersion is subjected to centrifugation at 2000 rpm during 60 min and the sedimented solid washed with EtOAc and dried. 57 mg are obtained. It is shown using TGA (see ex. 6: weight loss 250 to 600° C.: 26%, theory: 23%) that the solid is pure intercalated Nanofil EXM 588 with compound 101 and does not contain polymer.

The supernatant solution is evaporated and dried. According to TGA analysis the composition contains approximately 10% layered silicate and 90% polymer.

The X-ray analysis of the solid gave only peaks at $2\Theta > 10°$, which indicates complete exfoliation. A sample (150 mg) of this solid is refluxed with 15 ml 0.1 M LiBr solution in THF during 17 h at 65° C., to cleave off the polymer from the sheet silicate. After filtration molar mass ($M_n$) and PDI is determined by GPC in THF (relative to PS-standards): $M_n$=18000, $M_w$=38600, PDI=2.15.

The supernatant solution can be centrifuged during many hours (2000 rpm, corresponding to ca. 850 g), without further sedimentation. Even after 10-fold dilution with EtOAC it is stable for months (no sedimentation observed) which proves the nm size of the particles, indicating complete exfoliation.

Comparative Example D-Com

The experiment is performed in analogy to example 1 using 0.5 g with α,α'-azodiisobutyramidine-dihydrochloride intercalated Nanofil EXM588 in 9.5 g n-butyl acrylate, without further solvent. Polymerization: 3 h at 80° C. (bath temperature).

The dispersion is diluted with 240 ml toluene and 20 min centrifuged at 2000 rpm. After washing and drying 0.35 g of a solid is obtained which corresponds according to TGA analysis to pure with α,α'-azodiisobutyramidine-dihydrochloride intercalated Nanofil EXM588 and contains no polymer!

The supernatant solution is completely evaporated and the residue dissolved in 150 ml THF. Centrifugation 1 h with 2000 rpm gives again 50 mg with α,α'-azodiisobutyramidine-dihydrochloride intercalated Nanofil EXM588. After evaporation of all solvent and drying 24 h at 60° C. in vacuum 2.0 g polymer with ca. 0.1 g with α,α'-azodiisobutyramidine-dihydrochloride intercalated Nanofil EXM5881 is obtained in accordance with the TGA analysis: Weight loss 25° to 600° C.: 97% (calculated: 96.5%).

A sample (150 mg) of this solid is refluxed with 15 ml 0.1 M LiBr solution in THF during 17 h at 65° C. in order to seperate the polymer from the sheet silicate. Afterwards the solution is filtered and $M_n$ and PDI determined by GPC in THF (relative to PS-standards): $M_n$=658000, $M_w$=1360000, PDI=2.06.

The comparison of inventive example D1 with comparative example D-Com shows that the exfoliation of the layered silicate using intercalated NOR (ex. 1) followed by controlled radical polymerization is much more efficient: Firstly a much higher monomer conversion (85% compared to 20%) is obtained; secondly only a small amount of the layered silicate is not exfoliated (11.4% compared with 80% in ex. 1), which can be explained by an efficient initiation in all layers, and thirdly the formed polymer has a much lower, controlled molecular weight.

Example D2

In analogy to example D1, the controlled radical polymerization of styrene is used to exfoliate the sheet silicate Nanofil EXM588, intercalated with the cationic NOR compound 104. The exfoliated sheet silicate contains 66 wt. % polystyrene and 34 wt. % sheet silicate as measured by TGA. The attached (onto the sheet silicate layers) polystyrene has a molecular weight of $M_n$=2050, $M_w$=4010 (GPC analysis).

Example D3

In analogy to example D1, 10 g with compound 104 intercalated Nanofil EXM588 (ex. 7), 40 g n-butyl acrylate (BASF, techn. quality) and 120 g 2-methoxypropyl acetate is dispersed in a 350 ml round bottom flask with an ultraturax mixer during 25 min. After evacuation and purging 5 times with $N_2$, the monomer is polymerized during 18 h at 140° C. (oil bath temperature: 155° C.) with mechanical stirring. The monomer conversion, determined by $^1$H-NMR, is 33%. The dispersion is diluted with 100 ml EtOH and subjected to centrifugation at 2000 rpm during 60 min. 2 products, consisting of exfoliated sheet silicate with attached polymer are obtained:

The sedimented solid is redispersed in EtOH, centrifuged (1 h at 2000 rpm) and the sedimented product dried in high vacuum at 90° C. over night. 11.4 g of a grey solid is obtained. Weight loss measured by TGA (25° to 600° C., 10° C./min) gives 46 wt. % polymer attached to the sheet silicate (54 wt. %). In order to determine the molecular weight of the attached poly(n-butyl acrylate) chains, a sample (150 mg) of this solid is refluxed with 15 ml 0.1 M LiBr solution in THF during 17 h at 65° C. GPC gives a molar mass $M_n$ of 3380 and $M_w$=5150, corresponding to a PDI of 1.52 and therefore the polymerization is well controlled. The supernatant solution is also evaporated and dried: 18.75 g solid. Weight loss measured by TGA (25° to 600° C., 10° C./min) gives 60 wt. % polymer attached to the sheet silicate (40 wt. %). The determination of the molecular weight of the attached poly(n-butyl acrylate) chains by GPC gives a molar mass $M_n$ of 2340 and $M_w$=4140, corresponding to a PDI of 1.77. Also in this fraction, the polymerization is well controlled.

The X-ray analysis of both samples give only peaks at 2Θ>10°, indicating complete exfoliation.

Example D4

In analogy to example D3, 7.5 g with compound 111 intercalated Nanofil EXM588 (ex. 9), 40 g n-butyl acrylate (BASF, techn. quality) and 120 g 2-methoxypropyl acetate is dispersed in a 350 ml round bottom flask with an ultraturax mixer during 25 min. After evacuation and purging 5 times with $N_2$, the monomer is polymerized during 19 h at 140° C. (oil bath temperature: 155° C.) with mechanical stirring. The dispersion is put into a rotavap and all the solvents are evaporated. The highly viscous solid is than put into a Soxhlet extraction apparatus and continuously extracted with 300 ml EtOAc during 18 h. The remaining solid is dried in high vacuum at 90° C. over night: 15.5 g of a grey solid is obtained. Weight loss measured by TGA (25° to 600° C., 10° C./min) gives 64 wt. % polymer attached to the sheet silicate (36 wt. %). The determination of the molecular weight of the attached poly(n-butyl acrylate) chains by GPC gives a molar mass $M_n$ of 2530 and $M_w$=4090, corresponding to a PDI of 1.62, indicating a well controlled polymerization.

The extracted fraction (7.1 g) contained 86 wt. % polymer and 14 wt. % sheet silicate (TGA-analysis) and a molecular weight for the attached poly(n-butyl acrylate) chains of $M_n$ of 2470 and $M_w$=4070 (PDI=1.65).

In both fractions the polymerization is well controlled and the sheet silicate completely exfoliated (X-ray analysis).

Example D5

In analogy to example D4, 7.5 g with compound 111 intercalated Nanofil EXM588 (ex. 9), 32.5 g styrene (Fluka, purum) and 75 g butylacetate (Fluka, purum) is dispersed in a 350 ml round bottom flask with an ultraturax mixer during 25 min. After evacuation and purging 5 times with $N_2$, the monomer is polymerized during 24 h at 120° C. with mechanical stirring. The dispersion is precipitated in EtOH and the solid dried in a vacuum oven at 50° C. over night: 20 g of white solid. It is grinded to a fine powder and put put into a Soxhlet extraction apparatus and continuously extracted with 300 ml EtOAc during 18 h. The remaining solid is dried in high vacuum at 90° C. over night: 12.1 g of a grey solid is obtained. X-ray analysis shows complete exfoliation.

Weight loss measured by TGA (25° to 600° C., 10° C./min) gives 72 wt. % polymer attached to the sheet silicate (28 wt. %). The determination of the molecular weight of the attached poly(n-butyl acrylate) chains by GPC gives a molar mass $M_n$ of 4190 and $M_w$=4640, corresponding to a PDI of 1.11, indicating an extremely well controlled polymerization.

The extracted fraction is only 1.6 g, consisting of 82% polystyrene and only 18% sheet silicate, as measured by TGA. This fraction mostly contains well controlled polystyrene ($M_n$=3500, $M_w$=4230, PDI=1.21) which is not attached to the silicate layers. It is not used for test purposes. From the overall mass balance, the styrene conversion can be calculated to be ca. 31%.

Example D6

In analogy to example D4, 5 g with compound 111 intercalated Optigel SH, 25.8 g n-butyl acrylate (BASF, techn. quality) and 77.3 g 2-methoxypropyl acetate (Fluka, purum) is dispersed in a 350 ml round bottom flask with an ultraturax mixer during 25 min. After evacuation and purging 5 times with $N_2$, the monomer is polymerized during 19 h at 140° C. with mechanical stirring. The dispersion is put into a rotavap and all the solvents are evaporated. The paste is than put into a Soxhlet extraction apparatus and continuously extracted with 300 ml EtOAc during 18 h. The remaining solid is dried in high vacuum at 90° C. over night: 6.4 g of a white solid is obtained. X-ray analysis shows complete exfoliation. Weight loss measured by TGA (25° to 600° C., 10° C./min) gives 49 wt. % polymer attached to the sheet silicate (51 wt. %). The determination of the molecular weight of the attached poly (n-butyl acrylate) chains by GPC gives a molar mass $M_n$ of 3270 and $M_w$=5140, corresponding to a PDI of 1.57, indicating a well controlled polymerization.

The extracted fraction (5.2 g) consists of almost pure polymer, not attached to sheet silicate layers. From the mass balance, the n-butyl acrylate conversion can be calculated to be ca. 32%, leading to a theoretical (=calculated) molecular weight of the poly(n-butyl acrylate) chains of $M_n$=3270. This is in perfect agreement with the observed molecular weight and corroborates again the perfect control of the polymer chain length by this method.

The invention claimed is:

1. A process for preparing a monomer/polymer clay nanocomposite dispersion comprising the steps of
   A) providing a first aqueous dispersion of a natural or synthetic clay which can be partially intercalated and/or exfoliated and wherein said clay has an exchangeable cation; adding to said dispersion a compound of formula Ia, Ib, Ic, Id, Ie, II, IIIa, IIIb, IIIc, IIId, IIIe, IVa, Va, Vb, Vc, Vd or Ve and exchanging said cation at least partially and
   B) adding to said dispersion at least one ethylenically unsaturated monomer and polymerizing at least a portion of said ethylenically unsaturated monomer, wherein formula Ia, Ib, Ic, Id, Ie, II, IIIa, IIIb, IIIc, IIId, IIIe, IVa, Va, Vb, Vc, Vd and Ve are

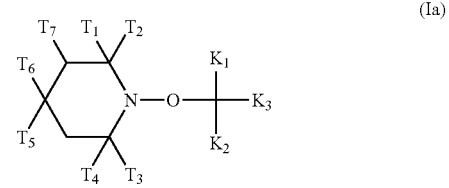

(Ia)

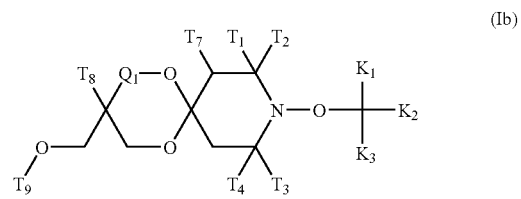

(Ib)

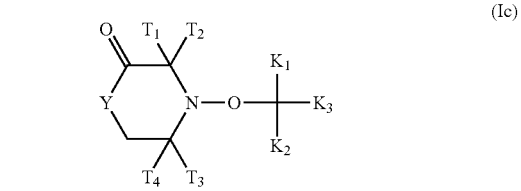

(Ic)

-continued

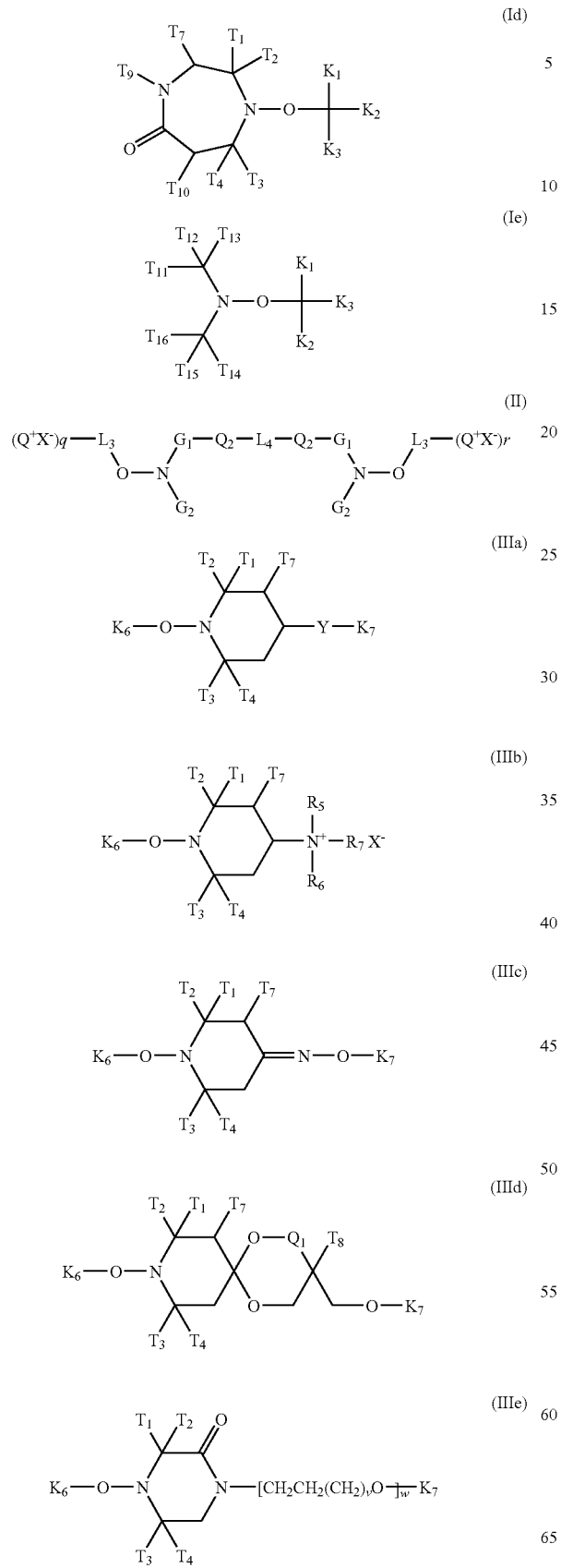
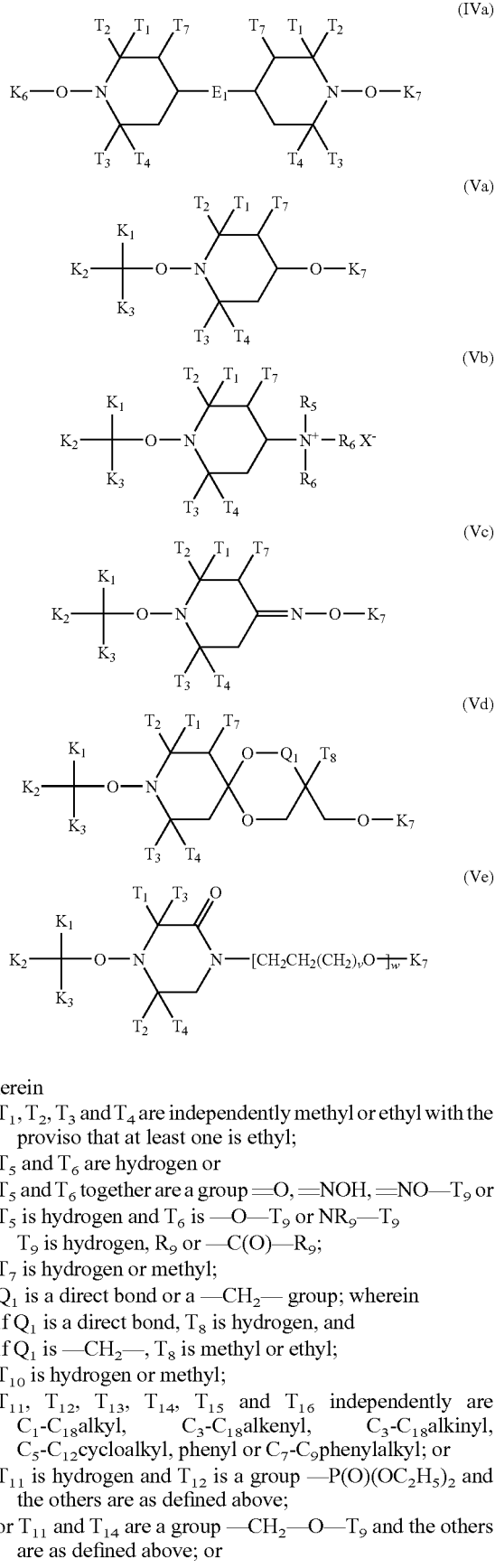

wherein
T$_1$, T$_2$, T$_3$ and T$_4$ are independently methyl or ethyl with the proviso that at least one is ethyl;
T$_5$ and T$_6$ are hydrogen or
T$_5$ and T$_6$ together are a group =O, =NOH, =NO—T$_9$ or
T$_5$ is hydrogen and T$_6$ is —O—T$_9$ or NR$_9$—T$_9$
T$_9$ is hydrogen, R$_9$ or —C(O)—R$_9$;
T$_7$ is hydrogen or methyl;
Q$_1$ is a direct bond or a —CH$_2$— group; wherein
if Q$_1$ is a direct bond, T$_8$ is hydrogen, and
if Q$_1$ is —CH$_2$—, T$_8$ is methyl or ethyl;
T$_{10}$ is hydrogen or methyl;
T$_{11}$, T$_{12}$, T$_{13}$, T$_{14}$, T$_{15}$ and T$_{16}$ independently are C$_1$-C$_{18}$alkyl, C$_3$-C$_{18}$alkenyl, C$_3$-C$_{18}$alkinyl, C$_5$-C$_{12}$cycloalkyl, phenyl or C$_7$-C$_9$phenylalkyl; or
T$_{11}$ is hydrogen and T$_{12}$ is a group —P(O)(OC$_2$H$_5$)$_2$ and the others are as defined above;
or T$_{11}$ and T$_{14}$ are a group —CH$_2$—O—T$_9$ and the others are as defined above; or $T_{16}$ is a group —C(O)—Y—$R_5$ and the others are as defined above; or $T_{11}$, $T_{12}$ and $T_{13}$ are a group —CH$_2$OH;

Y is O or NR$_9$;

v is a number from 0 to 10 and w is 0 or 1;

$K_1$ and $K_2$ are hydrogen, $C_1$-$C_{18}$alkyl, $C_5$-$C_{12}$cycloalkyl, phenyl or $C_7$-$C_9$phenylalkyl and $K_3$ is a group

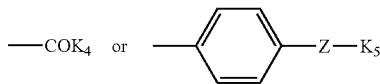

where $K_4$ is Y—[(CH$_2$—CH$_2$)—(CH$_2$)$_s$—N$^+$R$_5$R$_6$X$^-$]$_t$—CH$_2$—CH$_2$—(CH$_2$)$_s$—N$^+$R$_5$R$_6$R$_7$X$^-$ or —Y—CH$_2$—CHOH—CH$_2$—N$^+$R$_5$R$_6$X$^-$—{[(CH$_2$—CH$_2$)—(CH$_2$)$_s$—N$^+$R$_5$R$_6$X$^-$]$_t$—CH$_2$—CH$_2$—(CH$_2$)$_s$—N$^+$R$_5$R$_6$R$_7$X$^-$}$_u$, where s and t are each a number from 0-4 and u is 1; or

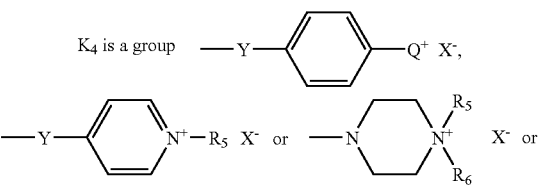

Z is —C(O)— or a direct bond, wherein if Z is —C(O)—, $K_5$ has the meaning of $K_4$, and if Z is a direct bond, $K_5$ is O—CH$_2$—CHOH—CH$_2$—N$^+$R$_5$R$_6$X$^-$—{[(CH$_2$—CH$_2$)—(CH$_2$)$_s$—N$^+$R$_5$R$_6$X$^-$]$_t$—CH$_2$—CH$_2$—(CH$_2$)$_s$—N$^+$R$_5$R$_6$R$_7$X$^-$}$_u$, Q$^+$X$^-$, —CH$_2$Q$^+$X$^-$ or —CHCH$_3$Q$^+$X$^-$;

$K_7$ is a group

—CH$_2$—CHOH—CH$_2$—N$^+$R$_5$R$_6$X$^-${[(CH$_2$—CH$_2$)—(CH$_2$)$_s$—N$^+$R$_5$R$_6$X$^-$]$_t$—CH$_2$—CH$_2$—(CH$_2$)$_s$—N$^+$R$_5$R$_6$R$_7$X$^-$}$_u$, where s and t are each a number from 0-4 and u is 1; or a group —D$_1$—Q$^+$X$^-$ where D$_1$ is $C_1$-$C_{12}$alkylene, $C_1$-$C_{12}$alkylene which is interrupted by one or more O, S, or NR$_9$ atoms, $C_5$-$C_{12}$cycloalkylene or phenylene;

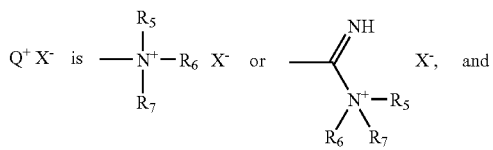

$R_1$ is $C_1$-$C_{18}$alkylene, $R_2$ is a direct bond or $C_1$-$C_{18}$alkylene, $R_3$ is hydrogen or $C_1$-$C_{18}$alkyl, $R_4$ is hydrogen or $C_1$-$C_{18}$alkyl, $R_5$, $R_6$ and $R_7$ are each independently of the others hydrogen, $C_1$-$C_{18}$alkyl, $C_3$-$C_{12}$cycloalkyl, phenyl or $C_7$-$C_9$phenylalkyl or $C_6$-$C_{10}$heteroaryl, which all may be unsubstituted or substituted by halogen, OH, NO$_2$, ON, $C_1$-$C_4$alkoxy, or $R_5$, $R_6$ and $R_7$ together with the nitrogen or phosphorous atom to which they are bonded form a 3-12 membered monocyclic or polycyclic ring which may contain further heteroatoms;

$R_9$ is hydrogen, $C_1$-$C_{18}$alkyl, $C_3$-$C_{18}$alkenyl, $C_3$-$C_{18}$alkinyl, phenyl, $C_7$-$C_9$phenylalkyl, which all may be unsubstituted or substituted by one or more hydroxy, halogen or $C_1$-$C_4$alkoxy groups $R_{22}$ is $C_1$-$C_{18}$alkyl;

X$^-$ is the anion of a $C_1$-$C_{18}$carboxylic acid which may contain more than one carboxylic acid group, fluoride, chloride, bromide, iodide, nitrite, nitrate, hydroxide, acetate, hydrogen sulfate, sulfate, $C_1$-$C_{18}$alkoxy sulfate, aromatic or aliphatic sulfonate, carbonate, hydrogen carbonate, perchlorate, chlorate, tetrafluoroborate, borate, phosphate, hydrogen phosphate, dihydrogen phosphate or mixtures thereof;

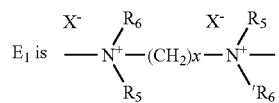

where x is a number from 2 to 12;

$K_6$ is selected from the group consisting of

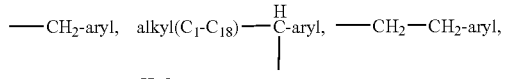

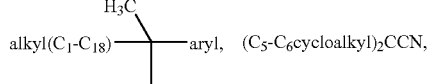

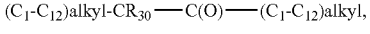

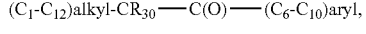

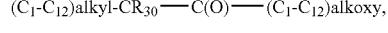

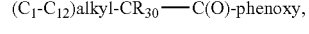

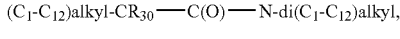

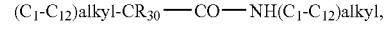

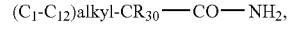

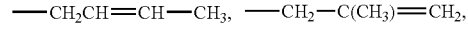

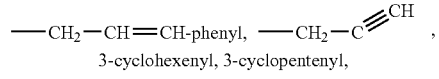

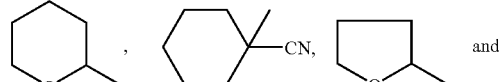

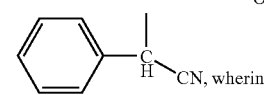

$R_{30}$ is hydrogen or $C_1$-$C_{12}$alkyl;

the alkyl groups are unsubstituted or substituted with one or more —OH, —COOH or C(O)R$_{30}$ groups; and the aryl groups are phenyl or naphthyl which are unsubstituted or substituted with $C_1$-$C_{12}$alkyl, halogen, $C_1$-$C_{12}$alkoxy, $C_1$-$C_{12}$alkylcarbonyl, glycidyloxy, OH, —COOH or —COO($C_1$-$C_{12}$)alkyl and wherein in formula II $G_1$ and $G_2$ independently represent a tertiary carbon atom to which an unsubstituted $C_1$-$C_{18}$alkyl or phenyl or with ON, $COC_1$-$C_{18}$alkyl, CO-phenyl, $COOC_1$-$C_{18}$alkyl, $OC_1$-$C_{18}$alkyl, $NO_2$, $NHC_1$—$C_{18}$alkyl or $N(C_1$-$C_{18})_2$alkyl substituted alkyl or phenyl groups are bonded; or one of $G_1$ and $G_2$ is a secondary carbon atom to which a group —P(O)(OR$_{22}$)$_2$ is bonded and the other is as defined above; or $G_1$ and $G_2$ together with the nitrogen atom to which they are bonded form a 5 to 8 membered heterocyclic ring or a polycyclic or spirocyclic 5 to 20 membered heterocyclic ring system which is substituted with 4 $C_1$-$C_4$alkyl groups or $C_5$-$C_{12}$ spirocycloalkyl groups in the ortho position to the nitrogen atom and which may be further substituted with one or more $C_1$-$C_{18}$alkyl, $C_1$-$C_{18}$alkoxy or =O groups; and which may be interrupted by a further oxygen or nitrogen atom;

with the proviso that at least one of the 4 $C_1$-$C_4$alkyl groups in ortho position to the nitrogen atom is higher alkyl than methyl;

$L_4$ is a linking group selected from the group consisting of a direct bond, $R_1$—Y or $R_2$—O(O)—Y— where Y is attached to $G_1$ and/or $G_2$; $C_1$-$C_{25}$alkylene, $C_2$-$C_{25}$alkylene interrupted by —O—, —S—, —SO—, —SO$_2$—, $$\diagdown_{N}^{\diagup}-R_3, \quad -\overset{O}{\underset{\|}{C}}-, \quad -\overset{O}{\underset{\|}{C}}-O-, \quad -\overset{O}{\underset{\|}{C}}-\underset{R_4}{N}-,$$

phenylene or $C_5$-$C_8$cycloalkylene;

$Q_2$ is a direct bond, O, $NR_5$ or $NR_5R_6$;

$L_3$ is a group containing at least one carbon atom and is such that the radical .$L_3(Q^+X^-)$ derived from the group is able to initiate polymerization of ethylenically unsaturated monomers;

and the group

—$L_3(Q^+X^-)$ in formula II is a group $$\diagdown_{K_2}^{K_1}\diagup^{K_3}.$$

2. A process according to claim 1 wherein the aqueous phase of step A) is at least partially removed before performing step B).

3. A process according to claim 1 wherein the compound is added in an amount of from 1% to 100% by weight, based on the weight of the clay.

4. A process according to claim 1 wherein the ethylenically unsaturated monomer or oligomer is selected from the group consisting of styrene, substituted styrenes, conjugated dienes, acrolein, vinyl acetate, vinylpyrrolidone, vinylimidazole, maleic anhydride, (alkyl)acrylic acid anhydrides, (alkyl) acrylic acid salts, (alkyl)acrylic esters, (meth)acrylonitriles, (alkyl)acrylamides, vinyl halides, vinylidene halides and mixtures thereof.

5. A process according to claim 4 wherein the ethylenically unsaturated monomers are styrene, α-methyl styrene, p-methyl styrene or a compound of formula $CH_2$=C($R_a$)—(C=Z)—$R_b$ or $CH_2C(R_a)$—(C=S)—$R_b$, wherein $R_a$ is hydrogen or $C_1$-$C_4$alkyl, $R_b$ is $NH_2$, O$^-$(Me$^+$), glycidyl, unsubstituted $C_1$-$C_{18}$alkoxy, $C_2$-$C_{100}$alkoxy interrupted by at least one N and/or O atom, or hydroxy-substituted $C_1$-$C_{18}$alkoxy, unsubstituted $C_1$-$C_{18}$alkylamino, di($C_1$-$C_{18}$alkyl)amino, hydroxy-substituted $C_1$-$C_{18}$alkylamino or hydroxy-substituted di($C_1$-$C_{18}$alkyl)amino, —O—$CH_2$—$CH_2$—N($CH_3$)$_2$ or —O—$CH_2$—$CH_2$—N$^+$H($CH_3$)$_2$An$^-$; wherein An$^-$ is an anion of a monovalent organic or inorganic acid;
Me is a monovalent metal atom or the ammonium ion and.

6. A process according to claim 1 wherein an acid containing unsaturated monomer is added, which is selected from the group consisting of methacrylic anhydride, maleic anhydride, itaconic anhydride, acrylic acid, methacrylic acid, itaconic acid, maleic acid, fumaric acid, acryloxypropionic acid, (meth)acryloxypropionic acid, styrene sulfonic acid, ethylmethacrylate-2-sulphonic acid, 2-acrylamido-2-methylpropane, sulphonic acid; phosphoethylmethacrylate; the corresponding salts of the acid containing monomer, and combinations thereof.

7. A process according to claim 1 wherein step B) is repeated with a second ethylenically unsaturated monomer which is different from the first one, leading to a block copolymer.

8. A process according to claim 1 wherein the natural or synthetic clay is selected from the group consisting of montmorillonite, saponite, beidellite, montronite, hectorite, stevensite, vermiculite, kaolinite, hallosite, synthetic phyllosilicates, and combinations thereof.

9. A monomer/polymer clay nanocomposite dispersion obtained by a process according to claim 1.

10. A method of improving the properties of paints, coatings, inks, adhesives, reactive diluents or thermoplastic materials which comprises incorporating a monomer/polymer clay nanocomposite dispersion according to claim 9 therein.

11. A process according to claim 1 wherein the compound of formula Ia, Ib, Ic, Id, Ie, II, IIIa, IIIb, IIIc, IIId, IIIe, IVa, Va, Vb, Vc, Vd or Ve is a compound of formula IIa, IIb, IIc, IId or IIe (IIa)

$$K_3-\overset{K_1}{\underset{K_2}{C}}-O-\underset{\underset{T_3\ T_4}{|}}{\overset{\overset{T_2\ T_1\ T_7}{|}}{N}}-Y-\underset{\underset{A_2}{|}}{\overset{\overset{A_1}{|}}{\underset{}{}}}-D-\underset{\underset{A_2}{|}}{\overset{\overset{A_1}{|}}{\underset{}{}}}-Y-\underset{\underset{T_4\ T_3}{|}}{\overset{\overset{T_7\ T_1\ T_2}{|}}{N}}-O-\overset{K_1}{\underset{K_2}{C}}-K_3$$

-continued

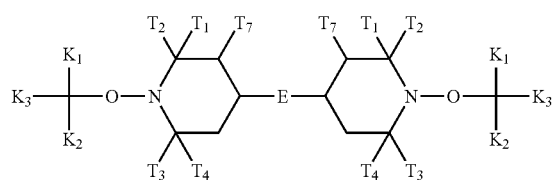
(IIb)

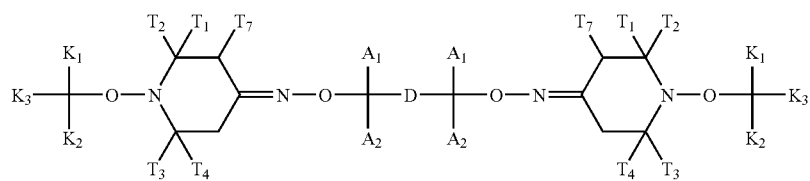
(IIc)

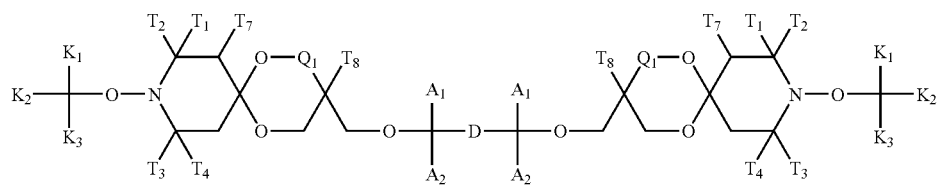
(IId)

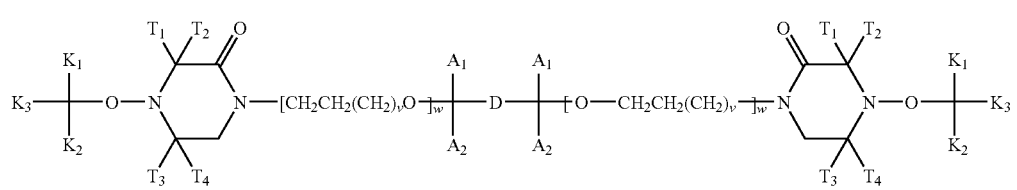
(IIe)

wherein $A_1$ and $A_2$ are independently hydrogen or together with the carbon atom to which they are bonded form a carbonyl group, —C(O)—;

D is a direct bond or $C_1$-$C_{12}$alkylene, $C_1$-$C_{12}$alkylene which is interrupted by one or more O, S, or $NR_9$ atoms, $C_5$-$C_{12}$cycloalkylene or phenylene;

E is a group —$NR_9$—$(CH_2)_x$—$NR_9$— where x is a number from 2 to 12, or a group

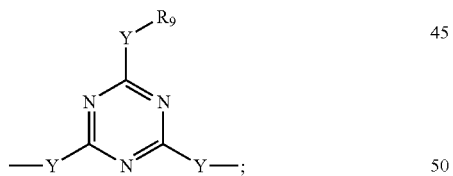

v is a number from 0 to 10 and w is 0 or 1.

12. A process according to claim 1 wherein the compound of formula Ia, Ib, Ic, Id, Ie, II, IIIa, IIIb, IIIc, IIId, IIIe, IVa, Va, Vb, Vc, Vd or Ve is a compound of formula Ia1, Ib1, Ic1, Id1 or Ie1

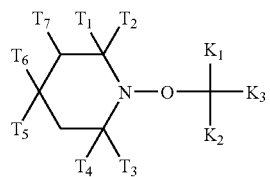
(Ia1)

-continued

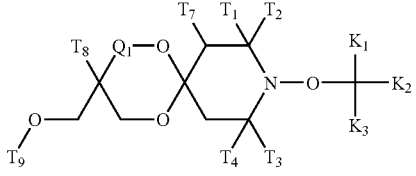
(Ib1)

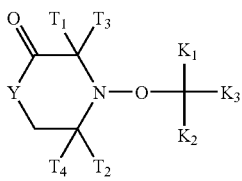
(Ic1)

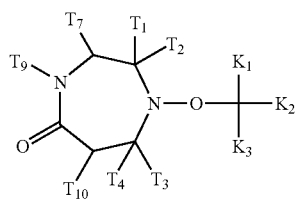
(Id1)

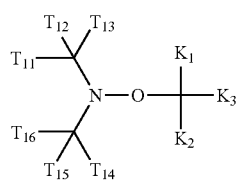
(Ie1)

wherein $Q_1$ is a direct bond or $CH_2$;

$T_1$ and $T_3$ are ethyl and $T_2$ and $T_4$ are methyl;

$T_7$ is methyl or H; $T_{10}$ is H if $T_7$ is methyl and $T_{10}$ is methyl if $T_7$ is H;

if $Q_1$ is a direct bond, $T_8$ is H;

if $Q_1$ is $CH_2$, $T_8$ is methyl or ethyl;

$T_{11}$, $T_{12}$, $T_{13}$, $T_{14}$, $T_{15}$ and $T_{16}$ are independently methyl or ethyl; or $T_{11}$ is H, $T_{12}$ is isopropyl, $T_{13}$ is phenyl and $T_{14}$, $T_{15}$, and $T_{16}$ are methyl; or $T_{11}$ is H, $T_{12}$ is —P(=O)(OC$_2$H$_5$)$_2$, $T_{13}$ is t-butyl and $T_{14}$, $T_{15}$, and $T_{16}$ are methyl; or $T_{11}$ and $T_{14}$ are —CH$_2$O—$T_9$ and $T_{12}$ and $T_{15}$ are methyl or phenyl and $T_{13}$ and $T_{16}$ are methyl or ethyl; or $T_{11}$, $T_{12}$, $T_{13}$, $T_{14}$, $T_{15}$ are methyl and $T_{16}$ is a group —CO—O—R$_9$ or —CON(R$_9$)$_2$; or $T_{11}$, $T_{12}$ and $T_{13}$ are —CH$_2$OH, $T_{14}$ is H, $T_{15}$ is isopropyl and $T_{16}$ phenyl;

$T_9$ is hydrogen, $R_9$ or —C(O)—R$_9$, where R$_9$ is hydrogen, $C_1$-$C_{18}$alkyl, $C_3$-$C_{18}$alkenyl, $C_3$-$C_{18}$alkinyl, phenyl or $C_7$-$C_9$phenylalkyl;

$K_1$ is H, $K_2$ is methyl or ethyl and $K_3$ is a group

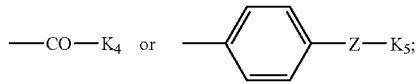

$K_4$ is —Y—CH$_2$—CH$_2$—(CH$_2$)$_s$—N$^+$X$^-$R$_5$R$_6$R$_7$ or; —Y—CH$_2$—CHOH—CH$_2$—N—CH$_2$—CH$_2$—(CH$_2$)$_s$—N$^+$X$^-$R$_5$R$_6$R$_7$ where Y is O or NR$_9$ and s is a number from 0 to 2;

if $K_3$ is

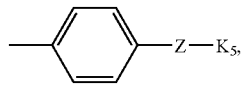

Z is —CO— or a direct bond; and if Z is —CO—, $K_5$ has the same meaning as $K_4$;

if Z is a direct bond, $K_5$ is a group —O—CH$_2$—CHOH—CH$_2$—N—CH$_2$—CH$_2$—(CH$_2$)$_s$—N$^+$X$^-$R$_5$R$_6$R$_7$ or —CH$_2$N$^+$R$_5$R$_6$R$_7$X$^-$.

13. A process for preparing a monomer/polymer clay nanocomposite dispersion comprising the steps of A) providing a first aqueous dispersion of a natural or synthetic clay which can be partially intercalated and/or exfoliated and wherein said clay has an exchangeable cation; adding to said dispersion a compound of formula VIa and exchanging said cation at least partially and B) adding to said dispersion at least one ethylenically unsaturated monomer and polymerizing at least a portion of said ethylenically unsaturated monomer, wherein formula VIa is

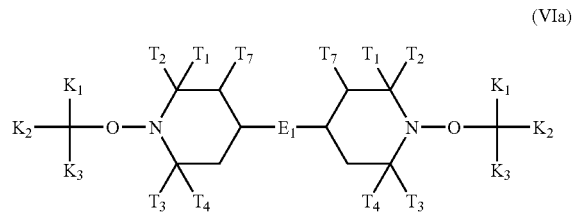

(VIa)

$T_1$, $T_2$, $T_3$ and $T_4$ are independently methyl or ethyl with the proviso that at least one is ethyl;

$T_7$ is hydrogen or methyl;

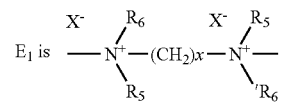

where x is a number from 2 to 12;

$R_5$ and $R_6$ are each independently of the others hydrogen, $C_1$-$C_{18}$alkyl, $C_3$-$C_{12}$cycloalkyl, phenyl or $C_7$-$C_9$phenylalkyl or $C_6$-$C_{10}$heteroaryl, which all may be unsubstituted or substituted by halogen, OH, NO$_2$, ON, $C_1$-$C_4$alkoxy;

X$^-$ is the anion of a $C_1$-$C_{18}$carboxylic acid which may contain more than one carboxylic acid group, fluoride, chloride, bromide, iodide, nitrite, nitrate, hydroxide, acetate, hydrogen sulfate, sulfate, $C_1$-$C_{18}$alkoxy sulfate, aromatic or aliphatic sulfonate, carbonate, hydrogen carbonate, perchlorate, chlorate, tetrafluoroborate, borate, phosphate, hydrogen phosphate, dihydrogen phosphate or mixtures thereof;

$K_1$ and $K_2$ are hydrogen, $C_1$-$C_{18}$alkyl, $C_5$-$C_{12}$cycloalkyl, phenyl or $C_7$-$C_9$phenylalkyl and $K_3$ is a group —COK$_4$ or

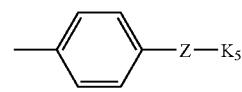

where $K_4$ is Y—[(CH$_2$—CH$_2$)—(CH$_2$)$_s$—N$^+$R$_5$R$_6$X$^-$]$_t$—CH$_2$—CH$_2$—(CH$_2$)$_s$—N$^+$R$_5$R$_6$R$_7$X$^-$ or —Y—CH$_2$—CHOH—CH$_2$—N$^+$R$_5$R$_6$X$^-$—{[(CH$_2$—CH$_2$)—(CH$_2$)$_s$—N$^+$R$_5$R$_6$X$^-$]$_t$—CH$_2$—CH$_2$—(CH$_2$)$_s$—N$^+$R$_5$R$_6$R$_7$X$^-$}$_u$, where s and t are each a number from 0-4 and u is 1; or $K_4$ is a group

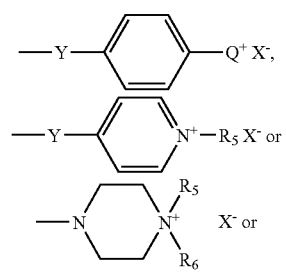

Z is —C(O)— or a direct bond, wherein if Z is —C(O)—, $K_5$ has the meaning of $K_4$, and if Z is a direct bond, $K_5$ is O—$CH_2$—CHOH—$CH_2$—$N^+R_5R_6X^-$—{[($CH_2$—$CH_2$)—$(CH_2)_s$—$N^+R_5R_6X^-]_t$—$CH_2$—$CH_2$—$(CH_2)_s$—$N^+R_5R_6R_7X^-$}$_u$, $Q^+X^-$, —$CH_2Q^+X^-$ or $CHCH_3Q^+X^-$; and

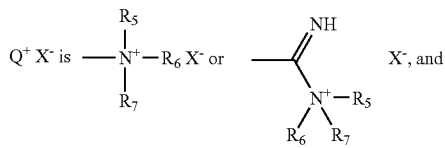

$R_7$ is hydrogen, $C_1$-$C_{18}$alkyl, $C_3$-$C_{12}$cycloalkyl, phenyl or $C_7$-$C_9$phenylalkyl or $C_6$-$C_{10}$heteroaryl, which all may be unsubstituted or substituted by halogen, OH, $NO_2$, CN, $C_1$-$C_4$alkoxy, or $R_5$, $R_6$ and $R_7$ together with the nitrogen or phosphorous atom to which they are bonded form a 3-12 membered monocyclic or polycyclic ring which may contain further heteroatoms.

14. A process for preparing a monomer/polymer clay nanocomposite dispersion comprising the steps of
  A) providing a first aqueous dispersion of a natural or synthetic clay which can be partially intercalated and/or exfoliated and wherein said clay has an exchangeable cation; adding to said dispersion a compound of formula IIa1, IIb1, IIc1 or IId1 and exchanging said cation at least partially and
  B) adding to said dispersion at least one ethylenically unsaturated monomer and polymerizing at least a portion of said ethylenically unsaturated monomer wherein formula IIa1, IIb1, IIc1 and IId1 are

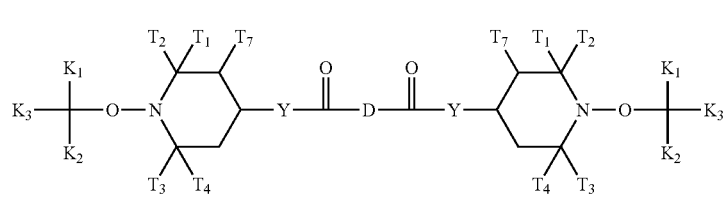

(IIa1)

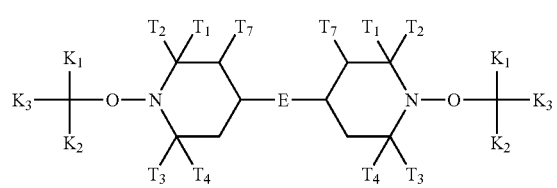

(IIb1)

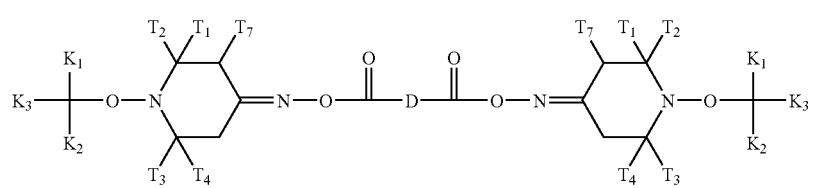

(IIc1)

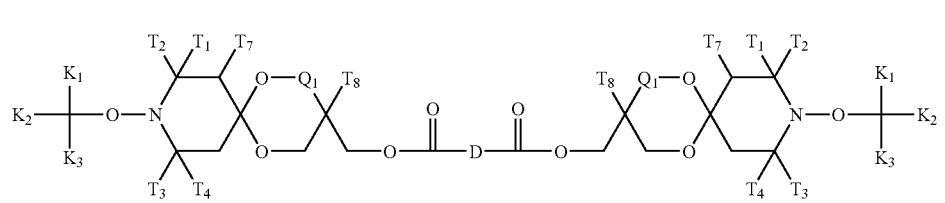

(IId1)

wherein
  $Q_1$ is a direct bond or $CH_2$;
  $T_1$ and $T_3$ are ethyl and $T_2$, $T_4$ and $T_7$ are methyl;
  if $Q_1$ is a direct bond, $T_8$ is H; and
  if $Q_1$ is $CH_2$, $T_8$ is methyl or ethyl;
  D is a direct bond, $C_1$-$C_{12}$alkylene or phenylene;
  E is —$NR_5$—$(CH_2)_x$—$NR_5$— where x is 2 to 12 or a group

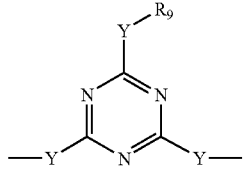

wherein Y is =$NR_9$;
  $K_1$ is H, $K_2$ is methyl or ethyl and
  $K_3$ is a group

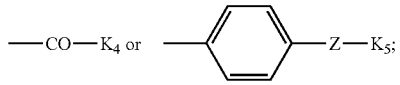

$K_4$ is —Y—$CH_2$—$CH_2$—$(CH_2)_s$—$N^+X^-R_5R_6R_7$ or —Y—$CH_2$—CHOH—$CH_2$—N—$CH_2$—$CH_2$—$(CH_2)_s$—$N^+X^-R_5R_6R_7$, where Y is O or $NR_9$ and s is a number from 0 to 2;
  $R_9$ is hydrogen, $C_1$-$C_{18}$alkyl, $C_3$-$C_{18}$alkenyl, $C_3$-$C_{18}$alkinyl, phenyl or $C_7$-$C_9$phenylalkyl;
  if $K_3$ is

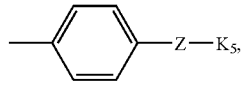

Z is —CO— or a direct bond;
  if Z is —CO—, $K_5$ has the same meaning as $K_4$;
  if Z is a direct bond, $K_5$ is a group —O—$CH_2$—CHOH—$CH_2$—N—$CH_2$—$CH_2$—$(CH_2)_s$—$N^+X^-R_5R_6R_7$ or —$CH_2N^+R_5R_6R_7X^-$;

and $X^-$ is the anion of a $C_1$-$C_{18}$carboxylic acid which may contain more than one carboxylic acid group, fluoride, chloride, bromide, iodide, nitrite, nitrate, hydroxide, acetate, hydrogen sulfate, sulfate, $C_1$-$C_{18}$alkoxy sulfate, aromatic or aliphatic sulfonate, carbonate, hydrogen carbonate, perchlorate, chlorate, tetrafluoroborate, borate, phosphate, hydrogen phosphate, dihydrogen phosphate or mixtures thereof.

15. A process according to claim 13 wherein the ethylenically unsaturated monomer or oligomer is selected from the group consisting of styrene, substituted styrenes, conjugated dienes, acrolein, vinyl acetate, vinylpyrrolidone, vinylimidazole, maleic anhydride, (alkyl)acrylic acid anhydrides, (alkyl)acrylic acid salts, (alkyl)acrylic esters, (meth)acrylonitriles, (alkyl)acrylamides, vinyl halides, vinylidene halides or mixtures thereof.

16. A process according to claim 14 wherein the ethylenically unsaturated monomer or oligomer is selected from the group consisting of styrene, substituted styrenes, conjugated dienes, acrolein, vinyl acetate, vinylpyrrolidone, vinylimidazole, maleic anhydride, (alkyl)acrylic acid anhydrides, (alkyl)acrylic acid salts, (alkyl)acrylic esters, (meth)acrylonitriles, (alkyl)acrylamides, vinyl halides, vinylidene halides and mixtures thereof.

17. A monomer/polymer clay nanocomposite dispersion obtained by a process according to claim 13.

18. A monomer/polymer clay nanocomposite dispersion obtained by a process according to claim 14.

\* \* \* \* \*

UNITED STATES PATENT AND TRADEMARK OFFICE
CERTIFICATE OF CORRECTION

PATENT NO. : 7,595,359 B2 Page 1 of 1
APPLICATION NO. : 10/519030
DATED : September 29, 2009
INVENTOR(S) : Mühlebach et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1255 days.

Signed and Sealed this

Twenty-eighth Day of September, 2010

David J. Kappos
*Director of the United States Patent and Trademark Office*